(12) United States Patent
Perkins et al.

(10) Patent No.: US 11,096,627 B2
(45) Date of Patent: Aug. 24, 2021

(54) MEDICAL EXAMINATION SYSTEM ENABLING INTERCHANGEABLE INSTRUMENT OPERATING MODES

(71) Applicant: Welch Allyn, Inc., Skaneateles Falls, NY (US)

(72) Inventors: David G. Perkins, Tully, NY (US); Raymond A. Lia, Auburn, NY (US); Robert L. Vivenzio, Auburn, NY (US); John R. Strom, Moravia, NY (US); Ervin Goldfain, Syracuse, NY (US); Steven R. Slawson, Camillus, NY (US); Michael T. McMahon, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 747 days.

(21) Appl. No.: 15/495,065

(22) Filed: Apr. 24, 2017

(65) Prior Publication Data
US 2017/0303857 A1    Oct. 26, 2017

Related U.S. Application Data

(60) Provisional application No. 62/327,154, filed on Apr. 25, 2016.

(51) Int. Cl.
*A61B 5/00* (2006.01)
*A61B 1/00* (2006.01)
(Continued)

(52) U.S. Cl.
CPC ........ *A61B 5/6898* (2013.01); *A61B 1/00105* (2013.01); *A61B 1/042* (2013.01); *A61B 1/227* (2013.01); *A61B 1/233* (2013.01); *A61B 1/303* (2013.01); *A61B 3/12* (2013.01); *A61B 5/0077* (2013.01); *F16B 1/00* (2013.01); *H04N 7/185* (2013.01); *A61B 1/267* (2013.01);
(Continued)

(58) Field of Classification Search
CPC .... A61B 5/6898; A61B 5/0077; G03B 17/565
See application file for complete search history.

(56) References Cited

U.S. PATENT DOCUMENTS 6,065,837 A     5/2000  Goldfain et al.
6,155,973 A *  12/2000  Howes ............... G02B 23/2484
                                                              359/683

(Continued)

OTHER PUBLICATIONS

International Search Report and Written Opinion for PCT/US2017/029322; dated Oct. 17, 2017; 18 pages.

*Primary Examiner* — Rajeev P Siripurapu
(74) *Attorney, Agent, or Firm* — Barclay Damon LLP

(57) ABSTRACT

An examination system having separate enabled interchangeable operating modes includes at least one medical device having a housing retaining an optical system. The examination system further includes an adapter that is configured for aligning a plurality of disparate smart devices with the optical system of the medical device when the adapter is attached to the medical device, thereby enabling multiple operating modes without modification to the device. In at least one version, common engagement features are provided on a plurality of medical devices to permit the adapter and an attached smart device to be used therewith interchangeably.

15 Claims, 26 Drawing Sheets

(51) Int. Cl.

| | | |
|---|---|---|
| *A61B 1/04* | (2006.01) | |
| *A61B 1/227* | (2006.01) | |
| *A61B 1/233* | (2006.01) | |
| *A61B 1/303* | (2006.01) | |
| *A61B 3/12* | (2006.01) | |
| *F16B 1/00* | (2006.01) | |
| *H04N 7/18* | (2006.01) | |
| *A61B 3/14* | (2006.01) | |
| *A61B 1/267* | (2006.01) | |

(52) U.S. Cl.
CPC ............... *A61B 3/1208* (2013.01); *A61B 3/14* (2013.01); *A61B 2560/0443* (2013.01); *A61B 2562/0233* (2013.01); *F16B 2001/0035* (2013.01)

(56) References Cited

U.S. PATENT DOCUMENTS

| | | | |
|---|---|---|---|
| 7,354,399 B2 | 4/2008 | Strom et al. | |
| 7,399,275 B2 | 7/2008 | Goldfain et al. | |
| 8,197,403 B2 | 6/2012 | Strom et al. | |
| 8,944,596 B2 | 2/2015 | Wood et al. | |
| 2004/0062545 A1* | 4/2004 | Ushiro | G03B 17/00 396/529 |
| 2008/0154091 A1* | 6/2008 | Dejima | A61B 17/29 600/104 |
| 2012/0262540 A1* | 10/2012 | Rondinelli | H04N 5/23238 348/36 |
| 2012/0320340 A1* | 12/2012 | Coleman, III | A61B 3/10 351/208 |
| 2013/0063873 A1* | 3/2013 | Wodrich | G06F 1/26 361/679.01 |
| 2013/0300919 A1 | 11/2013 | Fletcher et al. | |
| 2014/0051923 A1 | 2/2014 | Mirza et al. | |
| 2014/0072189 A1* | 3/2014 | Jena | A61B 5/150358 382/128 |
| 2015/0042873 A1* | 2/2015 | Hunt | H04N 5/2254 348/373 |
| 2015/0103317 A1 | 4/2015 | Goldfain et al. | |
| 2015/0362828 A1* | 12/2015 | Patel | G03B 17/48 348/75 |
| 2016/0051142 A1* | 2/2016 | Howes | A61B 3/14 351/245 |
| 2016/0073875 A1 | 3/2016 | Goldfain et al. | |

\* cited by examiner

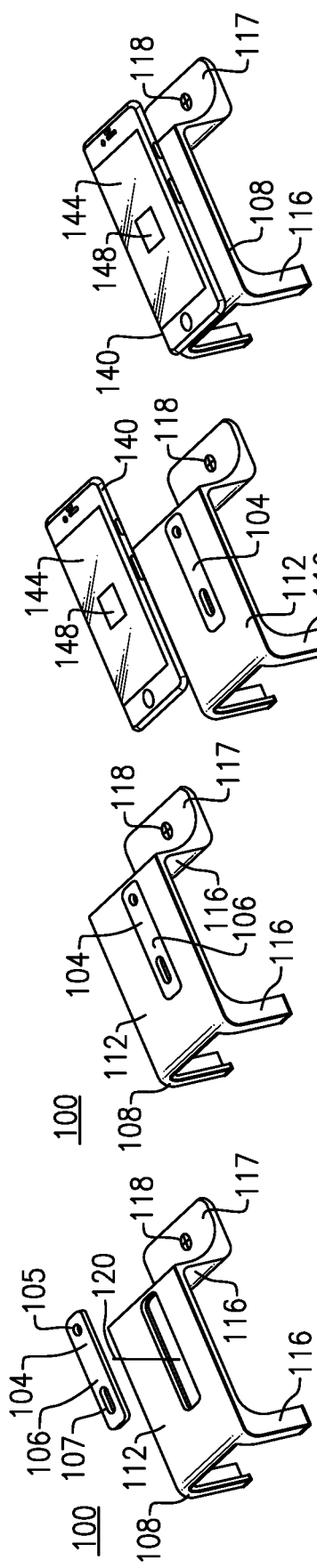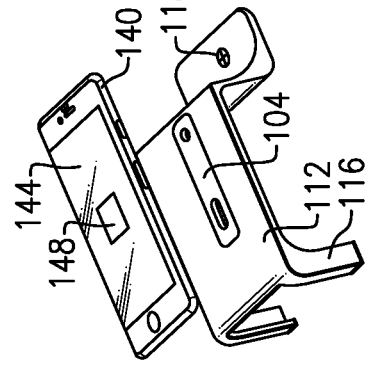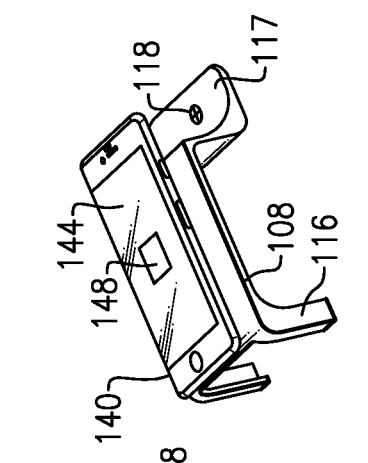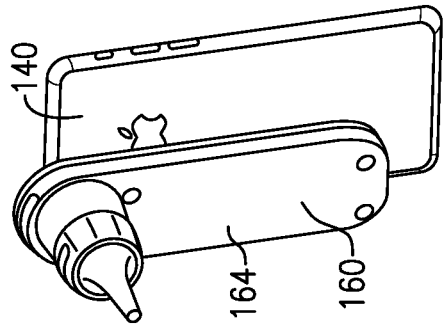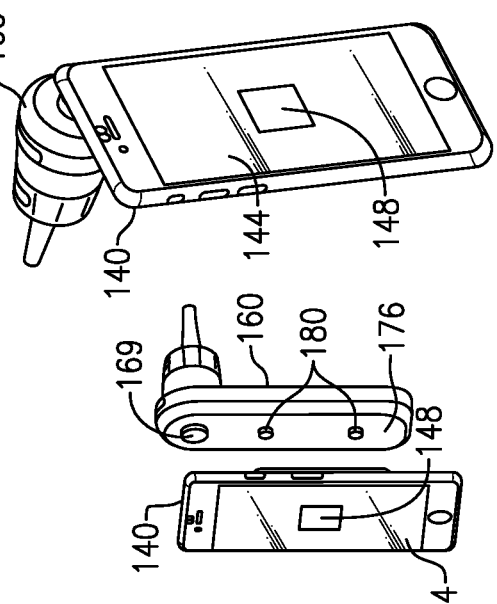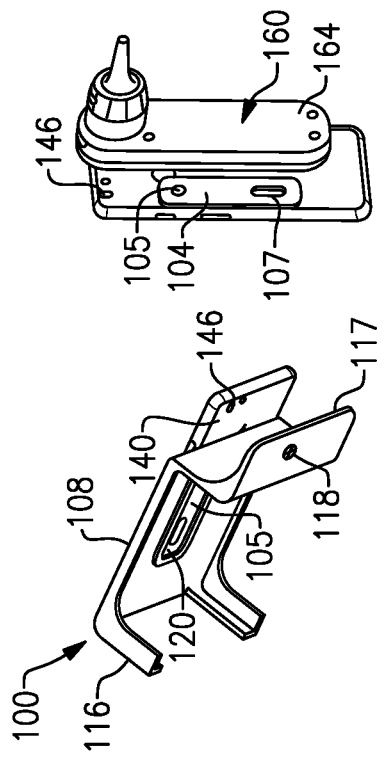

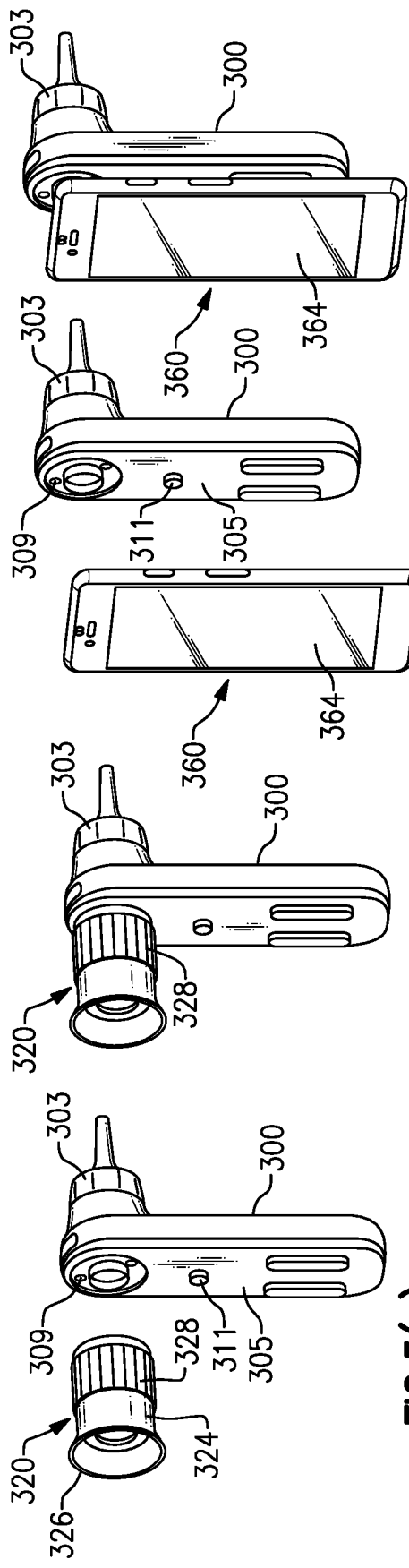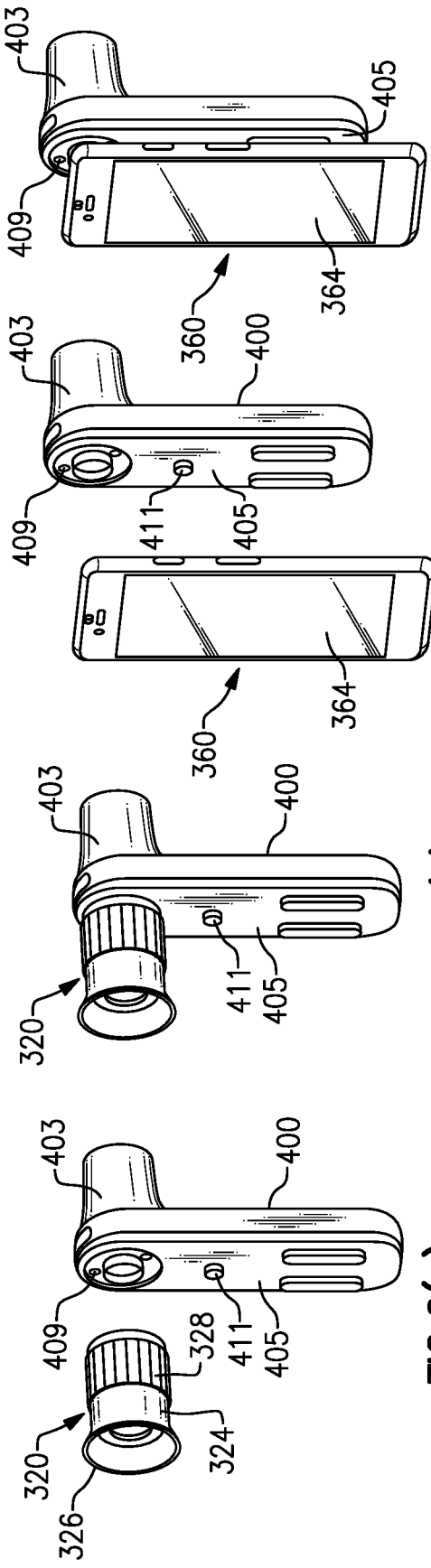

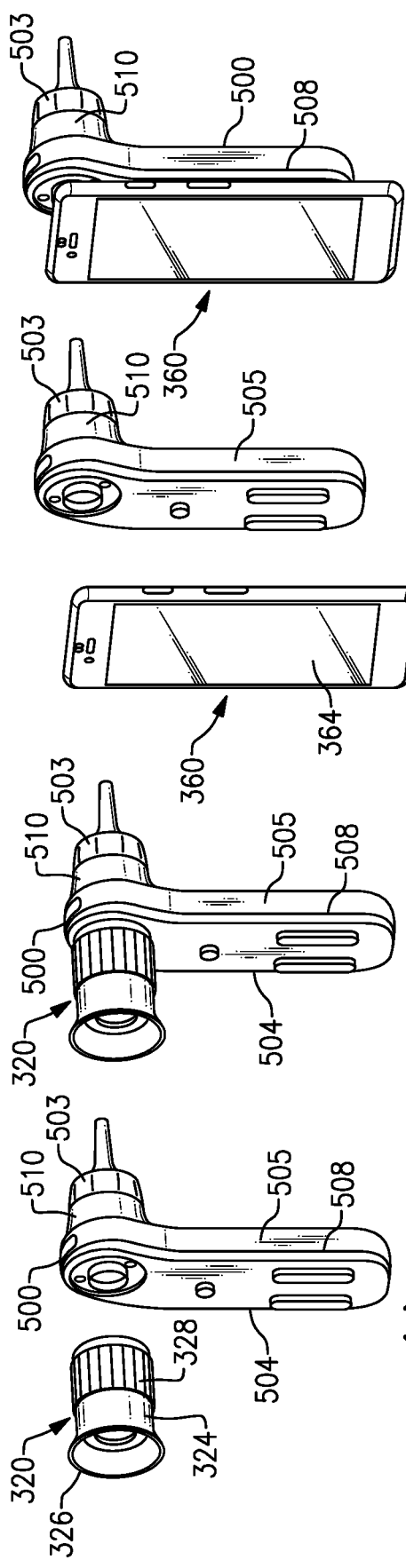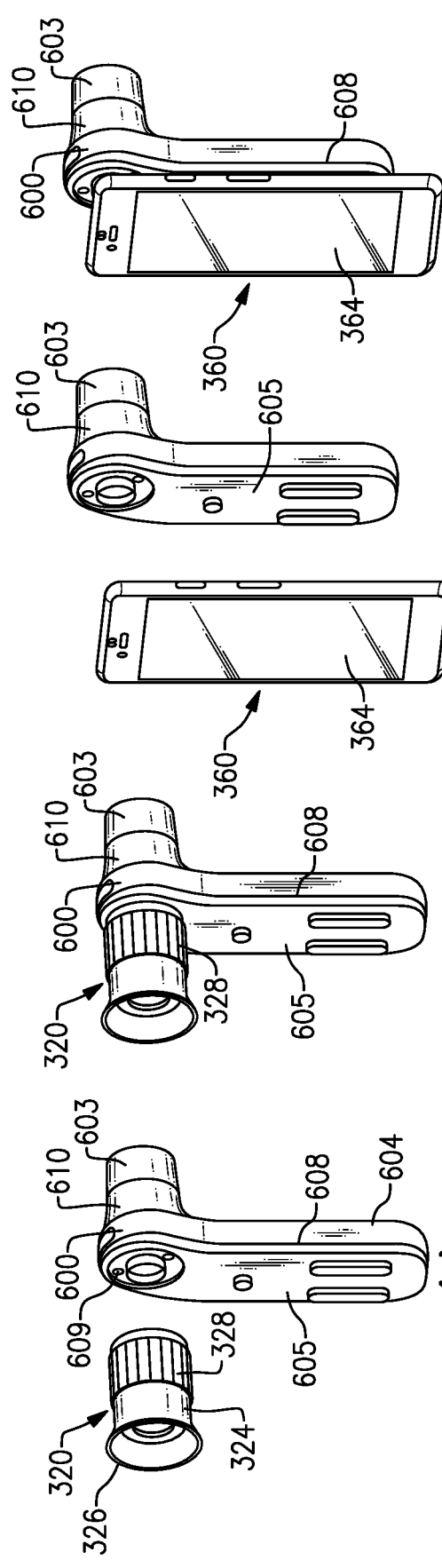

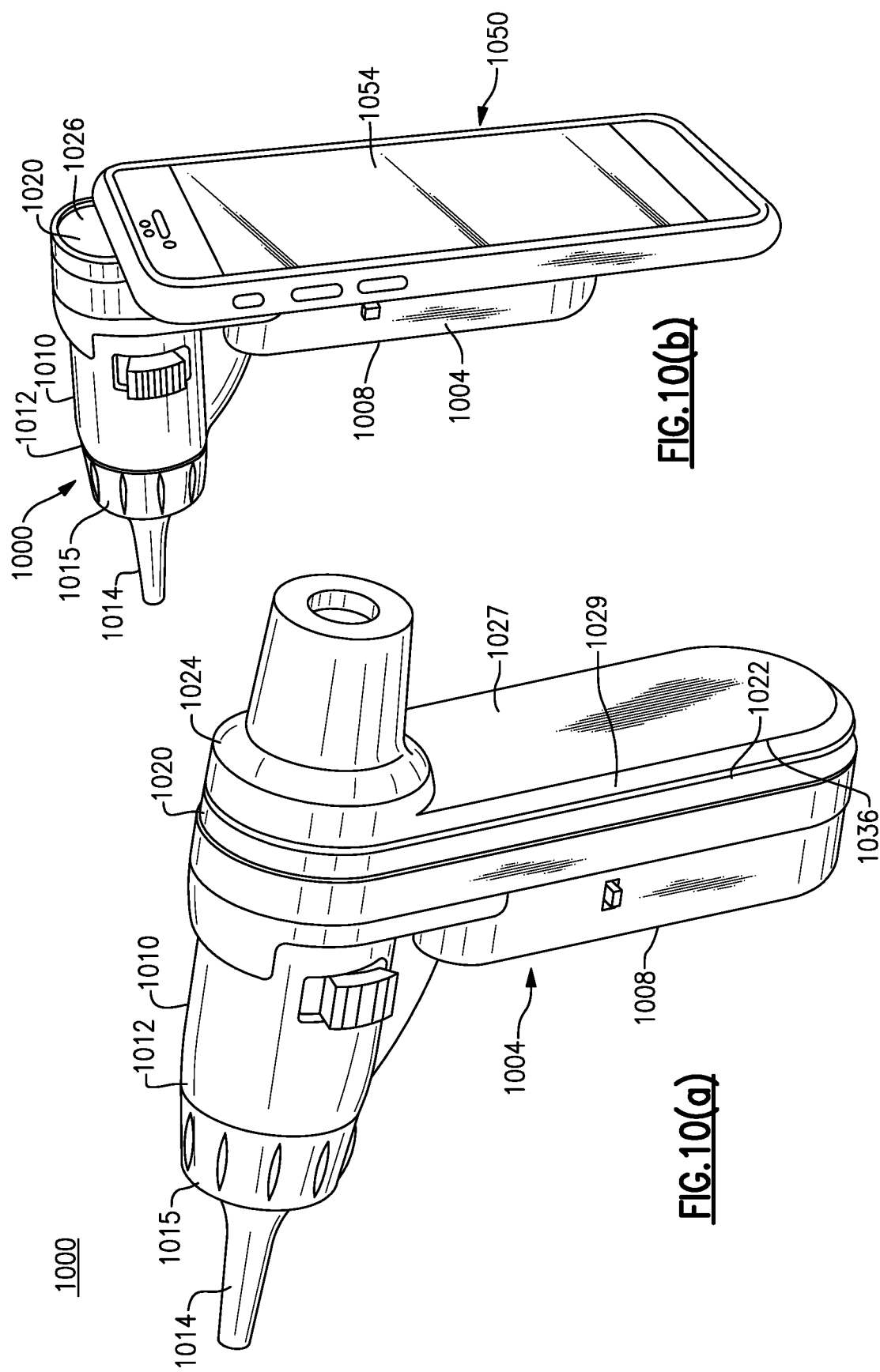

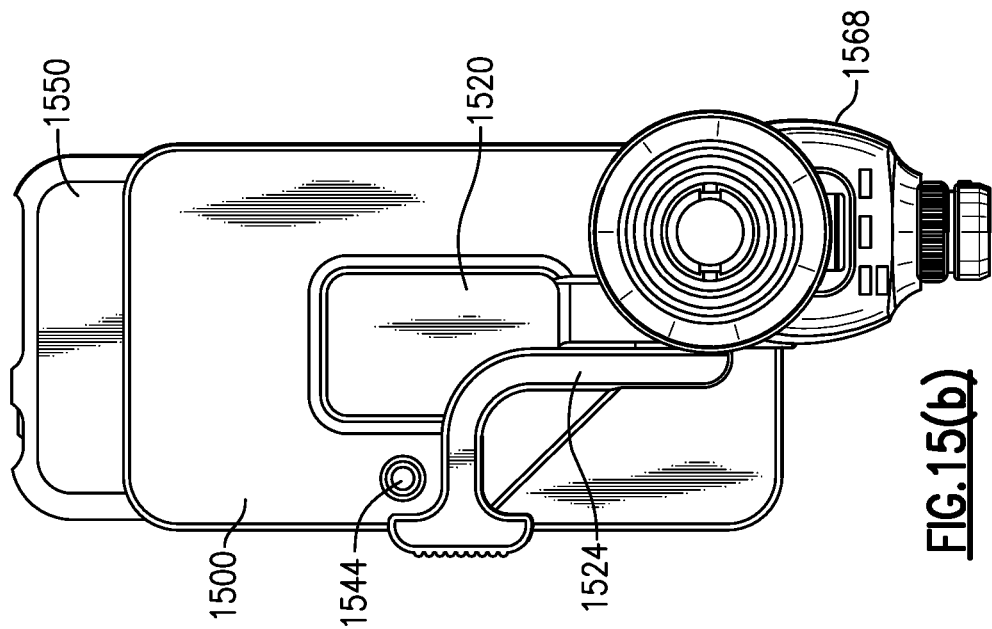
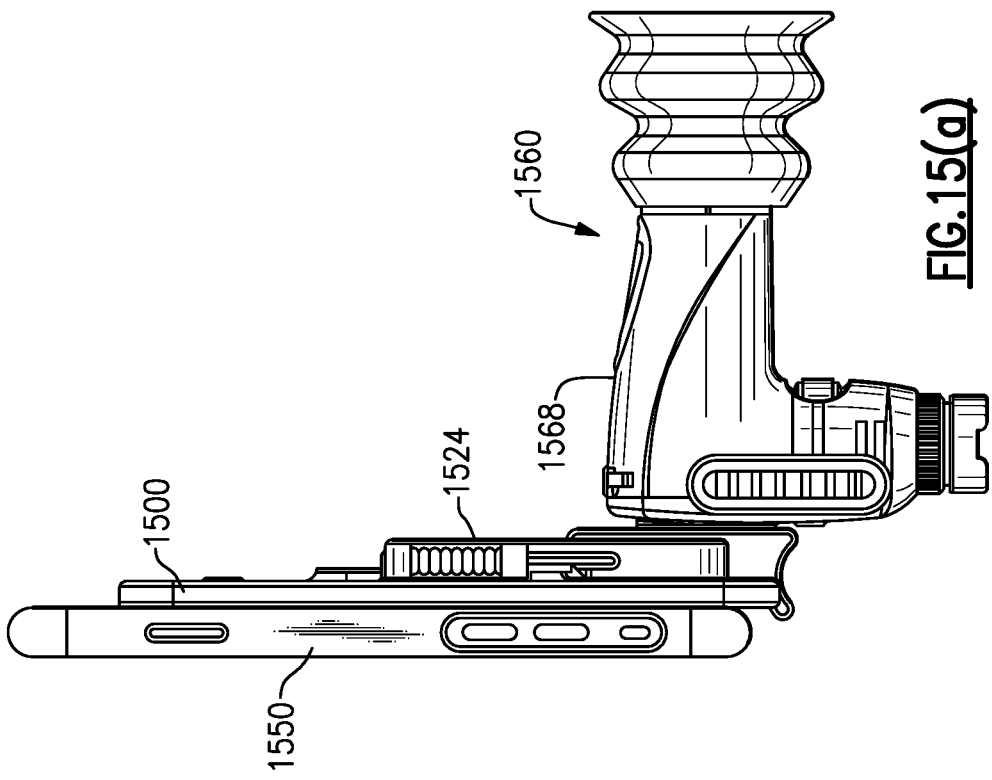

MEDICAL EXAMINATION SYSTEM ENABLING INTERCHANGEABLE INSTRUMENT OPERATING MODES

CROSS REFERENCE TO RELATED APPLICATION

Pursuant to relevant portions of 35 U.S.C. § 111 and 37 CFR § 1.53, this application claims priority to U.S. Patent Application No. 62/327,154, filed Apr. 25, 2016. This document is herein incorporated by reference in its entirety.

TECHNICAL FIELD

This application is generally directed to the field of diagnostic medicine and more specifically to a system having at least one stand-alone medical examination or diagnostic device, in which the device can assume or be configured to assume separate interchangeable operating modes. These modes can include a visual mode as well as an electronic viewing mode using an attached smart device. An adapter attached to the at least one medical examination or diagnostic device is configured to support and align one or one of a plurality of disparate smart devices relative to the optical axis of the medical device(s).

BACKGROUND

Hand-held diagnostic devices are well known in the medical field for purposes of conducting a patient examination, e.g., a wellness examination that would be typically conducted by a primary physician, physician's assistant (PA) or other health care provider, clinician, or caregiver. To that end, a number of disparate devices are routinely used for examining specific medical targets of interest, such as the eyes (ophthalmoscope), ears (otoscope), nose (rhinoscope), skin (dermatoscope), vagina (vagiscope and colposcope), anus (anoscope) and the like.

Some or all of these medical diagnostic instruments may include optical versions having an eyepiece disposed at one end of an instrument housing. Alternatively, electronic versions are also known having an electronic imager that captures a digital image of the intended medical target. More recently, so-called "smart devices", (e.g., smart phones, tablets and the like), have been incorporated for use with a medical examination or diagnostic device. One such example is the iExaminer® ophthalmoscope, which is manufactured and sold by Welch Allyn, Inc. of Skaneateles Falls, N.Y. Features relating to use of a smart device with a medical examination or diagnostic device herein are more completely described in greater detail in U.S. Pat. No. 8,944,596 B2 and U.S. Patent Application Publication No. 2015/0103317A1, the entire contents of each being herein incorporated by reference.

Reference is herein made to FIG. 1, which illustrates a known medical diagnostic device (i.e., an ophthalmoscope 10), which is configured to retain a smart device (more specifically, a smart phone). The ophthalmoscope 10 is defined by an instrument housing 14 that includes a distal end 16 and an opposing proximal end 18 and an interior sized and configured to retain a plurality of components. An optical system and an illumination system (not shown) are each retained within the interior of the instrument housing 14 and configured to enable viewing the eye of a patient (not shown). Features relating to a typical ophthalmoscope for use herein is more completely described in greater detail in U.S. Pat. No. 6,065,837, the entire contents of which is herein incorporated by reference.

A supporting fixture 20 fixedly secured to the proximal end 18 of the instrument housing 14 is configured to support an attached smart device 32. More specifically, the supporting fixture 20 is defined by a frame-like structure having an open top or upper end as well as a pair of parallel channels or slots 24 that are disposed along opposing lateral sides, enabling a specific smart device 32 (e.g., an iphone 4.0) to be releasably attached. The supporting fixture 20 further includes a cylindrically shaped nose section (not shown) made from a flexible material that is configured to fully cover the eyepiece of the ophthalmoscope 10. When the smart phone 32 is attached, the supporting fixture 20 retains the smart device 32 in a single defined position that provides the necessary alignment for the optics of the smart device 32 relative to the contained optical system (not shown) of the ophthalmoscope 10.

In use, the display of the attached smart device 32 is used to provide digital images of an intended medical target and in which a phone application stored into the memory of the smart phone 32 enables the instrument to be operated by a user. The supporting fixture 20 enables the optics of the smart phone 32 to be specifically aligned with the optical system of the ophthalmoscope 10, when the smart device 32 is attached thereto. A shortcoming of this system is that the supporting fixture 20 is only configured to adequately retain the specific smart device 32. Other smart devices cannot be similarly supported.

The foregoing is significant because alignment between the optics of an attached smart device and the optical system of a stand-alone medical diagnostic or examination device is critical to performance. Additionally, there is a general and pervasive need in the field of medical diagnostics to enable or provide medical examination or diagnostic devices with the capability of assuming a plurality of operating modes, as needed, so as to provide greater versatility.

BRIEF DESCRIPTION

Therefore and according to one aspect, there is provided a medical examination system comprising a medical device including a housing having an optical system within an interior of the housing. The optical system is defined by an optical axis and configured to operate in an optical viewing mode using an eyepiece. The system further comprises an adapter for aligning a digital camera of a smart device with the optical system of the medical device to enable a separate electronic operating mode, each of the adapter and the medical device having complementary features to permit attachment of the adapter to the medical device, the adapter having at least one feature configured to permit each of a plurality of different sized smart devices to be attached to the adapter and in alignment with the optical system of the medical device when the adapter is attached thereto.

According to at least one version, an aligning mechanism includes at least one interface plate interconnecting the smart device and the medical examination device. In an embodiment, the at least one interface plate can be secured, such as adhesively, to the housing of the smart device and in which the medical examination device is releasably attached to the secured at least one interface plate. A mount or alignment assembly or fixture can be provided in order to initially position the at least one interface plate relative to the smart device and in a predetermined location, the adapter having an portion configured to engage the at least one interface plate. Preferably, the interface plate is metal and the portion of the adapter includes at least one magnet for releasably securing the interface plate specifically thereon.

The medical device can include a proximal end having a device receiving portion that is configured to releasably engage a device connection portion of the adapter wherein the adapter includes an opening that is aligned with the camera aperture of the digital camera of the smart device when the smart device is attached via the at least one interface plate. The opening of the adapter is aligned with the viewing axis of the medical device when the adapter is attached to the medical device.

According to at least one version, the adapter includes a lever configured for releasing the adapter from the medical device. Additionally, the device connection portion of the adapter can include a spring-loaded pin that is movable into and out of a defined recess sized to engage the proximal receiving portion of the medical device, wherein the lever is movable to a position to release the pin and assist in releasing the adapter from the medical device.

When attached, the adapter can be moved to a plurality of mounting positions relative to the viewing or optical axis of the medical device. Moreover, the adapter positions the smart device at the convergence point of the eyepiece, thereby placing the smart device in the same position as the viewer's eye in the viewing mode.

A plurality of different medical examination or diagnostic devices can be provided, each of the medical devices having a proximal receiving portion that is configured for engaging the device connection portion of the adapter.

According to another aspect, there is provided an adapter configured for attachment to at least one medical device, the adapter comprising a support surface configured to retain one of a plurality of different sized smart devices. The support surface includes a portion that receives an alignment feature of each smart device to align the camera aperture of an attached smart device with a formed opening. Each of the plurality of smart devices includes a digital camera wherein the adapter, when attached, is configured to align the digital camera with the optical system of a medical examination device. The adapter further comprises a device connection portion configured for engaging a proximal receiving portion of a medical device such that, when attached, the opening of the adapter is aligned with the optical axis of the medical device.

The adapter can include at least one feature for enabling release of the adapter from the medical device such as a lever. In one version, the lever is configured to cooperate with a spring loaded pin of the proximal receiving portion of the medical device.

According to one version, the portion of the support surface includes at least one magnet for engaging the alignment feature of the smart device.

According to yet another aspect, there is provided a medical device comprising a housing, an optical system disposed within the housing including an eyepiece enabling an optical viewing mode; and a proximal receiving portion configured for engaging an adapter retaining a smart device to enable the medical device to assume an electronic imaging mode.

According to one version, the proximal receiving portion retains a set of eyepiece optics. The proximal receiving portion can be defined in at least one embodiment as a cylindrical section having a channel and a lipped portion configured for releasably engaging a device connection portion of the adapter supporting the smart device.

The medical device can be at least one of a plurality of disparate medical diagnostic instruments including at least one from the group consisting essentially of dermatoscopes, otoscopes, ophthalmoscopes, colposcopes, rhinoscopes, each of the instruments being configured to engage the adapter.

According to yet another aspect, a medical instrument examining system comprises a first medical examination device having a distal end, a proximal end and an optical system aligned along an optical axis and a second medical examination device having a distal end, a proximal end and an optical system aligned along an optical axis. Each of the first and second medical examination devices has a proximal receiving portion configured for releasably engaging a device connection portion of the adapter and in which the adapter includes an opening that is aligned with the optical axis of the first and second medical examination device when the adapter.

The adapter includes a supporting member configured to retain a smart device having a camera, the adapter being configured for retaining the smart device such that the camera of the smart device is automatically aligned with the opening of the adapter and the optical axis of the first and second medical examination devices.

One advantage realized by the herein described medical examination system is greater versatility by permitting interchangeable attachment of an eyepiece and an electronic device, such as a smart device, with at least one stand-alone medical examination device. In the inventive system, for example, a number of smart devices can be separably attached and aligned with the optics contained within at least one or more discrete stand-alone medical devices using a generic adapter and an interface that permits the adapter to be connected without modification to a number of medical devices.

Another advantage provided by the herein described system is that either minor or no modifications are required to enable the interchangeable operating modes and in which the adapter used enables repeatable alignment between the optical elements of the stand-alone medical device and the eyepiece or smart device.

These and other features and advantages will be readily apparent from the following Detailed Description, which should be read in conjunction with the accompanying drawings.

BRIEF DESCRIPTION OF THE DRAWINGS

Various features and advantages of the present invention will become more apparent when taken in conjunction with the following description and drawings wherein identical reference numerals have been used, where possible, to designate identical features that are common to the figures, and wherein:

FIG. 2(a) is a top perspective view of an alignment assembly in accordance with an embodiment, the alignment assembly including an alignment fixture and an interface plate;

FIG. 2(b) is the top perspective view showing the alignment fixture of FIG. 2A with a retained interface plate;

FIG. 2(c) is a perspective view of a smart device disposed in relation to the alignment fixture of FIGS. 2(a) and 2(b);

FIG. 2(d) is a top perspective view of the smart device on the alignment fixture of FIGS. 2(a)-2(c) for purposes of attaching the interface plate thereto;

FIG. 2(e) is a bottom perspective view of the alignment assembly of FIG. 2(d);

FIG. 2(f) is a front perspective view showing the attachment of a stand-alone medical diagnostic or examination device to a smart device using the attached interface plate of FIGS. 2(a)-2(e);

FIG. 2(g) is a rear perspective view showing the attachment of the smart device of FIG. 2(f) to the stand-alone medical diagnostic or examination device;

FIG. 2(h) is a rear perspective view of the stand-alone medical diagnostic or examination device and attached smart device of FIGS. 2(f) and 2(g), including a display relating to optical alignment;

FIG. 2(l) is another top perspective view of the alignment fixture of FIGS. 2(j) and 2(k);

FIGS. 5(a)-5(d) depict rear perspective views of a medical instrument assembly showing various assembled and unassembled operating modes between a first stand-alone medical device, an eyepiece, and a smart device in which the eyepiece and smart device can be interchangeably attached to the first stand-alone medical device to enable the various operating modes;

FIGS. 6(a)-6(d) depict rear perspective views of another medical instrument assembly showing various assembled and unassembled operating modes between a second stand-alone medical device, an eyepiece and a smart device in which the eyepiece and smart device are interchangeably attached to the second stand-alone medical device to enable the various operating modes;

FIGS. 7(a)-7(d) depict rear perspective views of yet another medical instrument assembly showing various assembled and unassembled operating modes between another stand-alone medical device, an eyepiece and a smart device in which the eyepiece and smart device are interchangeably attached to the stand-alone medical device to enable the various operating modes;

FIGS. 8(a)-8(d) depict rear perspective views of still another medical instrument assembly showing various assembled and unassembled operating modes between another stand-alone medical device, an eyepiece and a smart device in which the eyepiece and smart device are interchangeably attached to the depicted stand-alone medical device in order to enable the various operating modes;

FIG. 10(a) is a perspective view of a medical examination device made in accordance with another embodiment and configured to provide an optical viewing mode;

FIG. 10(b) is a perspective view of the medical examination device of FIG. 10(a) having an attached smart device, the medical examination device being configured in an electronic viewing mode;

FIG. 15(a) is a side elevational view of a medical examination device supporting a smart device using the adapter of FIGS. 14(a)-14(c);

FIG. 15(b) is a front facing view of the medical examination device of FIG. 15(a)

DETAILED DESCRIPTION

Figure 1:
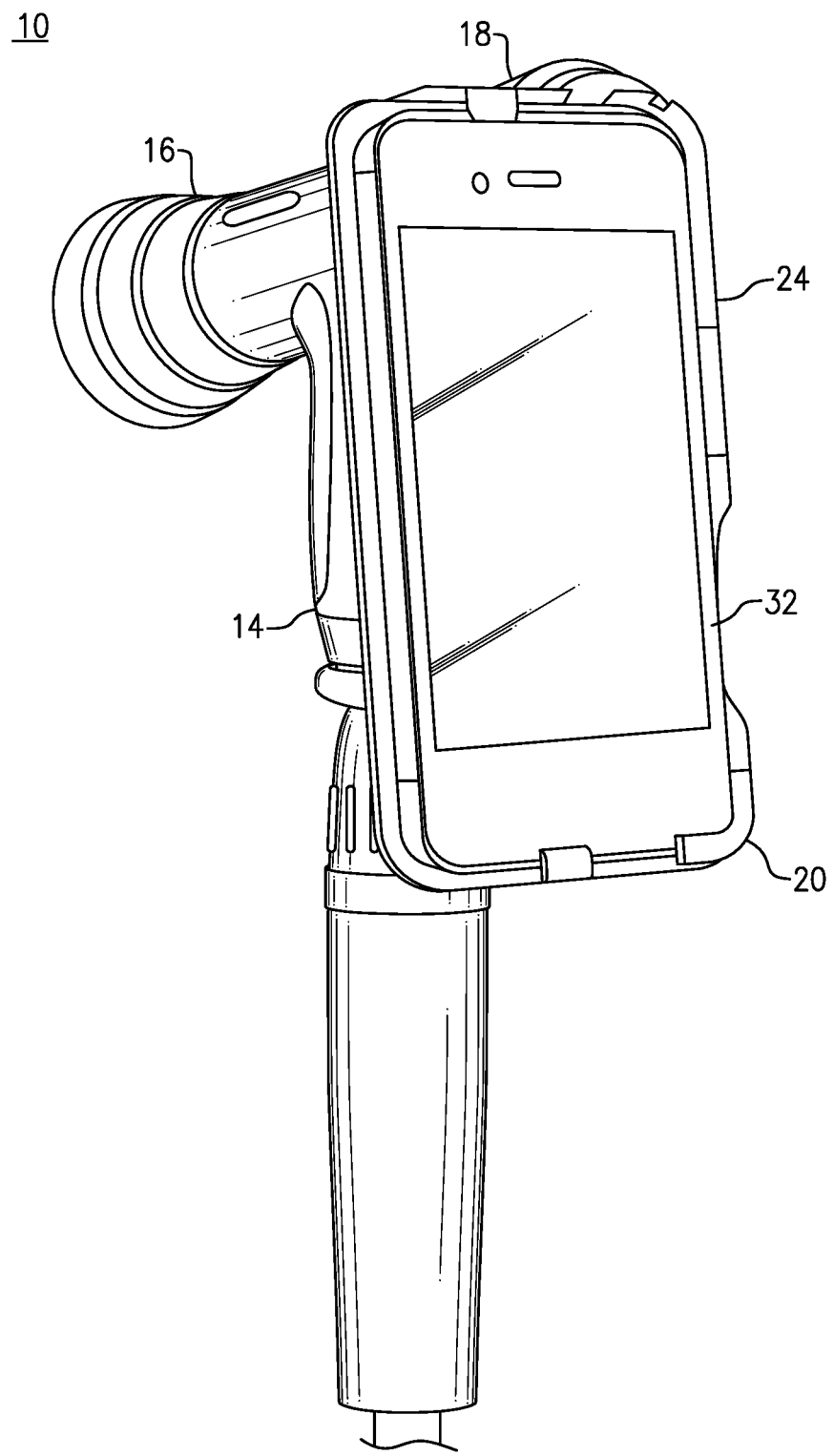
FIG. 1 is a perspective view of a stand-alone medical diagnostic or examination device having a smart device attached thereto in accordance with a previously known attachment fixture or frame.

The following description relates to certain embodiments of a medical examination system that includes at least one stand-alone medical diagnostic or examination device that is configured for operation in a number (at least two (2)) of interchangeable operating modes. In at least one version, an adapter is configured to generically support one of a plurality of smart devices, such as smart phones, in which the generic adapter is further configured to be attached to one of a plurality of disparate medical examination devices. In another version, a plurality of medical devices are configured with a common or generic interface enabling a smart device to be used interchangeably with the medical devices.

For purposes of explanation, the specific medical examination or diagnostic devices described in the following embodiments include otoscopes for examining the ears of a patient and ophthalmoscopes for examining aspects of the eyes of a patient. However, it will be readily apparent that the concepts discussed herein are further applicable to a varied number of other stand-alone medical diagnostic or examination instruments or devices, such as but not limited to dermatoscopes, vagiscopes, colposcopes, and anoscopes, among other devices capable of viewing of a medical target of interest.

In addition, the following description utilizes a number of terms for the purpose of providing an adequate or suitable frame of reference in relation to the accompanying drawings. These terms, which may include "inner", "outer", "external", "internal", "distal", "proximal", "above", "below", "top", "bottom" and the like should not be interpreted as necessarily limiting the intended scope of the invention, including the claims, unless so specifically indicated.

As used herein, the term "smart device" refers to any apparatus or device that is mobile and connected to other devices via wireless protocols or networks under IEEE 802.11 including but not limited to WiFi, Bluetooth, 3G and the like. The smart device as defined herein includes at least one electronic imaging device (e.g., a digital camera) and related optics, memory and a microprocessor capable of running application software, which may include but is not limited to smart phones and tablets.

As used herein, the term "stand-alone medical diagnostic or examination device" refers to an instrument used to view a medical target of interest of a patient which includes an optical system and optionally includes an illumination system. Examples of these devices may include but are not limited to otoscopes, ophthalmoscopes, dermatoscopes, vagiscopes and anoscopes for viewing a medical target of interest.

A system according to several embodiments is described herein and defined by at least one stand-alone medical diagnostic or examination device that can be used interchangeably using an interface that enables an optical mode as well as an electronic imaging mode. As discussed herein, each of the optical system of the medical device(s) and the camera of the smart device can be repeatably and reliably aligned to enable dual functionalities without significant modification to the stand alone diagnostic or examination device.

With reference to FIGS. 2(a) and 2(b) and according to a first embodiment, an alignment fixture 100 is provided that is used for indexing a smart device prior to attachment to a medical diagnostic or examination device. As discussed herein, the purpose of the fixture 100 is to provide placement of an interface or alignment plate(s) on a smart device. The positioning of the interface plate(s) enables proper alignment between the camera of the smart device and the optical system of a medical device to which the smart device is attached. The alignment fixture 100 according to the depicted version is defined by a raised platform 108 having a planar upper or top surface 112, as well as a plurality of legs 116 that extend downwardly from the upper surface 112. One of the legs 116 according to this embodiment includes a support flange 117 that further includes an optical target 118, such as a reticle. An elongate slot 120 formed in the top surface 112 of the alignment fixture 100 is sized and configured to receive an interface plate 104.

The interface plate 104 according to this specific embodiment is a substantially planar section made preferably from metal and including a through hole 105 and a slot 107, each aligned and spaced from one another. According to this embodiment, an upper side 106 of the interface plate 104 includes an adhesive layer to enable securement to the front facing surface 144 of a smart device 140 as shown in FIGS. 2(c)-2(e) using the alignment fixture 100. More specifically, the interface plate 104 is positioned within the elongate slot 120 of the alignment fixture 100, with the upper side 106 of the interface plate 105 facing upwardly. The smart device 140, which according to this embodiment is a smart phone, is then brought to the alignment fixture 100 with the front facing surface 144 of the smart device 140 facing the top surface 112 of the alignment fixture 100 and the contained camera 146 of the smart device 140 being aimed at the optical target 118.

As shown in these figures, the smart device 140 is activated by the user and an application stored into memory on the smart device 140 is configured to provide a target on the display 144, including a cross hair or other aiming means (e.g., a target 148) in order to verify that the optical target 118 is centered on the display 144. Once the target 148 is centered on the display 144 of the smart device 140, and as shown in FIGS. 2(d) and 2(e), the smart device 140 can be brought into contact with the adhesive layer 106 of the interface plate 104. The smart device 140 and attached interface plate 104 can be subsequently removed from the alignment fixture 100 by releasing the interface plate 104 from the retaining slot 120.

With reference to FIGS. 2(f)-2(i), the smart device 140 having the attached interface plate 104 can then be attached to a stand-alone medical diagnostic or examination device. According to this depicted embodiment, the stand-alone medical or examination device is an otoscope 160 that is used for viewing the outer and middle ear of a patient. The otoscope 160 is defined by a housing 164 that includes an instrument head attached to the upper end of a downwardly extending handle, the instrument head having a distal end and an opposing proximal end as well as an interior that is sized and configured to retain a number of optical elements. The distal end of the instrument head of the otoscope 160 includes a conical insertion portion that is configured to releasably receive a hollow speculum tip element, also having a conical configuration that is designed to be fitted only to a predetermined distance into the outer ear of a patient (not shown).

Figure 2J:
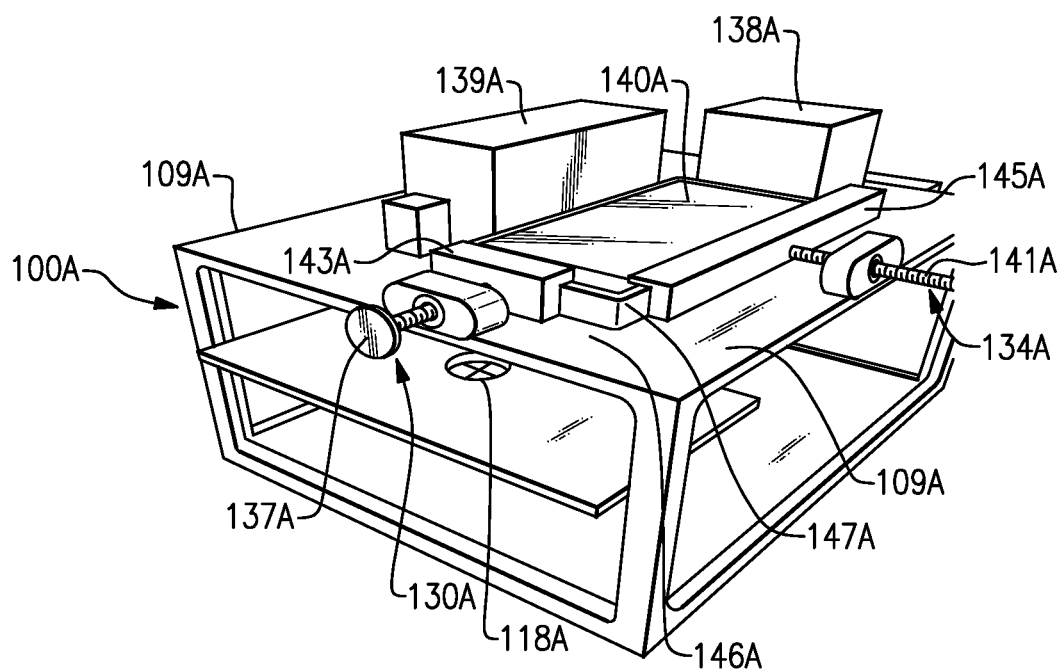
FIG. 2(j) is a top perspective view of an alignment fixture made in accordance with another embodiment.
Figure 2K:
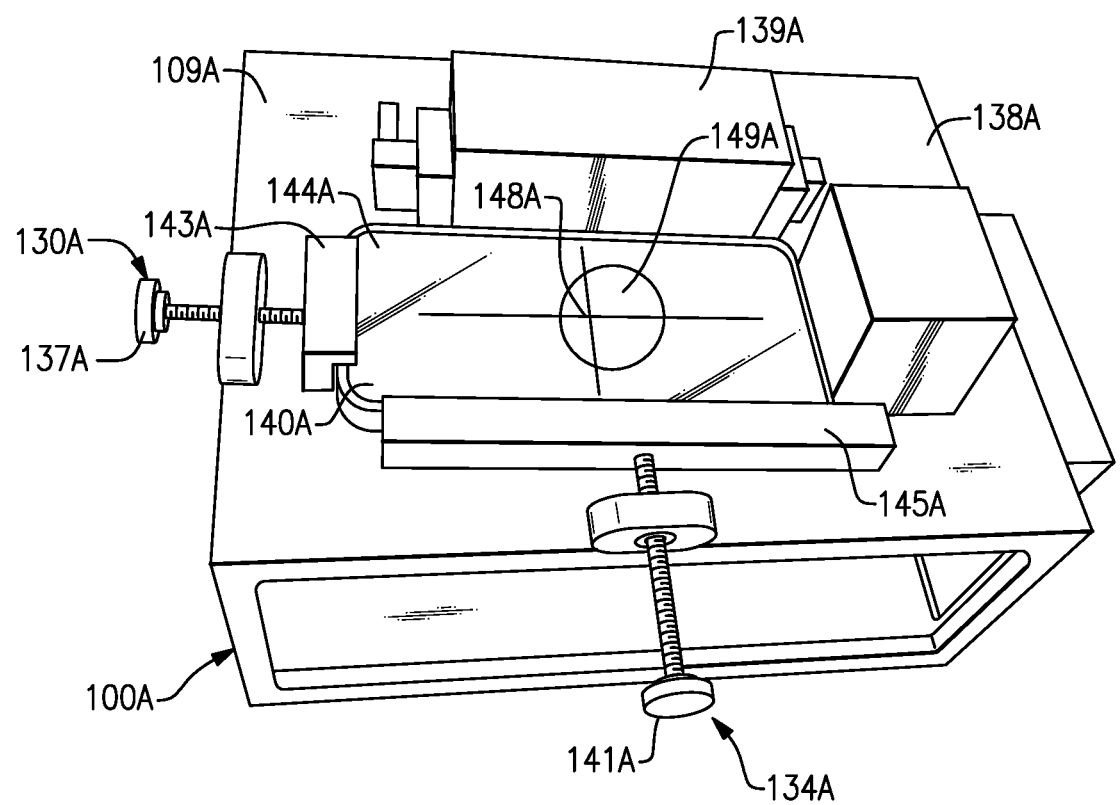
FIG. 2(k) is a side perspective view of the alignment fixture of FIG. 2(j)
Figure 2I:
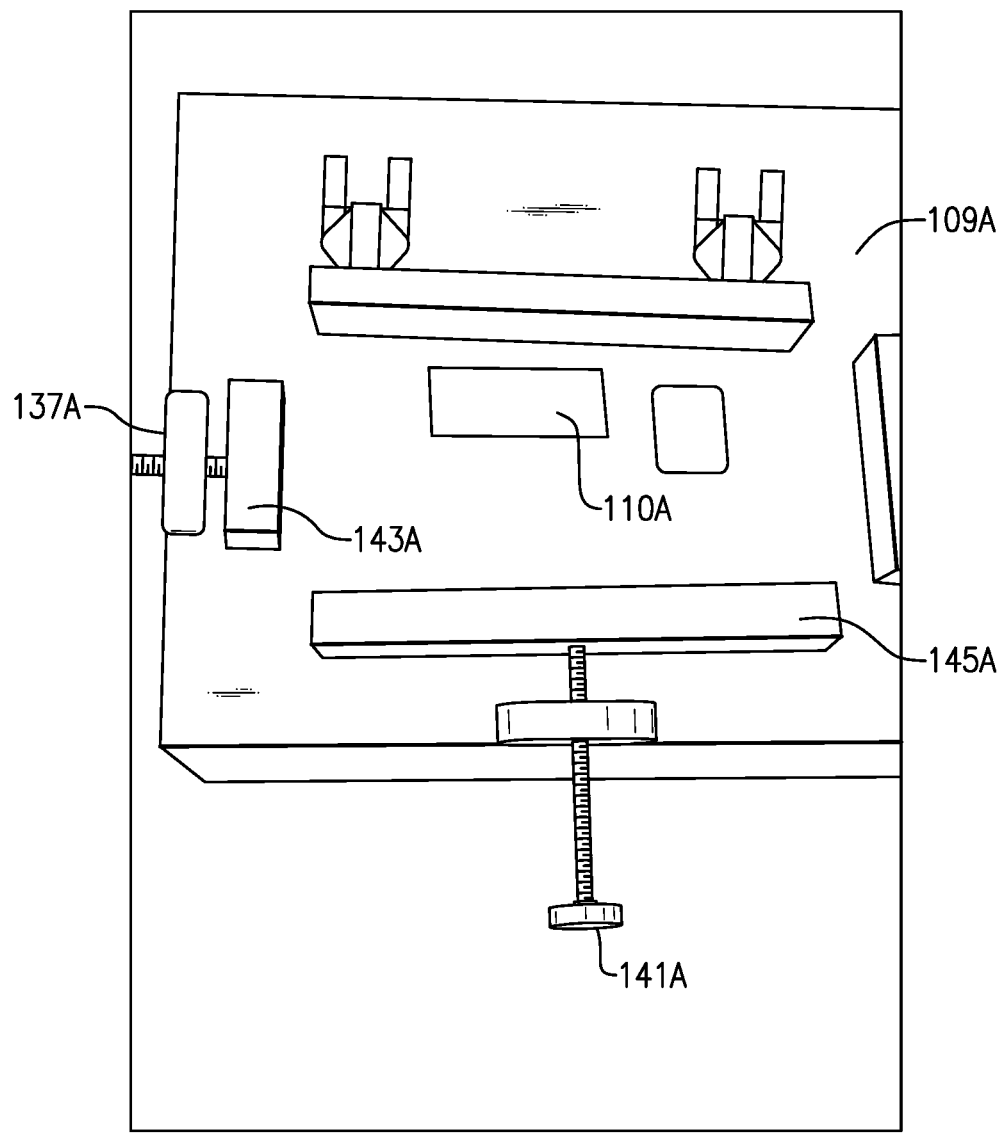
FIG. 2(i) is a front perspective view of the stand-alone medical diagnostic or examination device and attached smart device of FIGS. 2(f)-2(h)

According to this version, the rear or proximal facing side surface 176 of the instrument housing 164 includes a pair of spaced magnets 180. When assembled and as shown in FIGS. 2(h) and 2(i), the hole 105 and slot 107 of the fixedly secured interface plate 104 provides a specific and repeatable datum with regard to the smart device 140 to enable optical alignment when the smart device 140 is attached to the otoscope 160. When attached, the camera 146 of the attached smart device 140 is specifically aligned with the optical system of the otoscope 160 and more specifically a rear or proximal opening 169 of the instrument housing 164.

It will be understood that variations of the alignment fixture are also contemplated given the need determined by Applicants to precisely and very accurately align the interface plate properly onto a smart device for the herein described examination system. For example and as shown in FIGS. 2(j)-2(l), another alignment fixture 100A is depicted for purposes of aligning a smart device for positioning of at least one interface plate (not shown). The alignment fixture 100A, according to this version, is defined by a structure having a planar support surface 109A. Respective x-axis and y-axis adjustment assemblies 130A, 134A are engageable with lateral sides of a smart device, and more specifically a smart phone 140A that is positioned onto the top of the planar support surface 109A. According to this version, the interface place (not shown) can be placed within a shelf (not shown) located directly beneath the planar support surface 109A. More specifically, the interface plate(s) is positioned within a defined recess(es) or slot(s) (not shown) in the shelf with an exposed adhesive side of the interface plate(s) facing a slot 110A, FIG. 2(l), of the alignment fixture 100A.

According to this embodiment, the alignment fixture 100A includes respective x-axis and y-axis adjustment assemblies 130A and 134A that include respective spring-loaded adjustment or support blocks 138A and 139A, each set orthogonally to one another on the top of the planar support surface 109A. Respective x-axis and y-axis screw adjustment members 137A and 141A, according to this embodiment, are fixedly and threadingly disposed within the center of a corresponding beam-like member 143A and 145A in spaced parallel relation to the spring-loaded adjustment blocks 138A and 139A. Each of the beam-like members 143A, 145A further include a recessed interior portion 146A and 147A, respectively, that is sized to be placed onto and cover a lateral edge of a smart device (e.g., smart phone 140A) that is introduced onto the fixture 100A. When mounted, the relative position of the smart phone 140A can be laterally shifted wherein vertical movement is restricted by the beam-like members 143A, 145A, as well as the lateral support surface 109A of the alignment fixture 100A.

When the camera of the smart phone 140A is activated, an alignment application stored by the phone memory is programmed to display a set of cross hairs or other suitable target 148A. The smart phone 140A is then placed on the planar support surface 109A with the display side facing upwardly and the camera of the smart phone 140A aligned with a pinhole 111A, FIG. 2(l) formed on the planar support surface 109A that is aligned with an optical target 118A disposed beneath the planar support surface 109A. A back light (not shown) can be disposed beneath the optical target 118A to enhance illumination and visualization by the smart device 140A.

The smart phone 140A is initially set with lateral edges of the smart phone 140A being placed against the spring-loaded support blocks 138A and 139A. The screw adjustment members 137A, 141A and the beam-like members 143A, 145A are retracted sufficiently to allow the smart phone 140A to be initially positioned onto the planar support surface 109A. Once crudely positioned and aligned, the x-axis and y-axis adjustment members 130A, 134A are then moved into position using the screw adjustment members 137A, 141A with the beam-like members 143A, 145A, and more specifically the interior recessed portions 146A and 147A covering and engaging the lateral edges of the smart phone 140A. Fine adjustments can then be made against the bias of the spring loaded support blocks 138A, 139A to accurately center the image 149A of the optical target 118A on the display 144A and more specifically the cross hairs (target 148A) as needed, until the image 149A of an optical target 119A disposed beneath the planar support surface 109A is centered on the display 144A, and more specifically within the defined cross hairs 148A.

The above procedure can also detect misalignment and tolerancing issues of the smart device 140A and permit the image 149A of the optical target 118A to be as effectively and accurately centered relative to the cross hairs 148A on the display 144A as possible. Such tolerancing and misalignment issues are minor for typical use of the smart device, but are magnified when used for purposes of optically aligning to a medical diagnostic or examination device. Once centered, the shelf retaining the at least one interface plate can be pressed upwardly into contact with the front facing side of the smart device 140A, adhesively and reliably securing the at least one interface plate.

It will be understood that the alignment fixture 100A can be easily modified to accept smart devices having different configurations and footprints to permit optical alignment and placement of an interface plate(s) as herein described.

Figure 3:
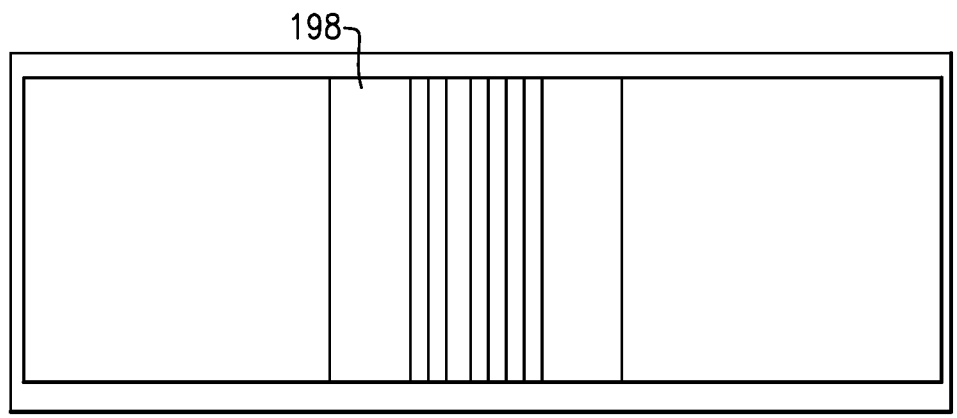
FIG. 3 depicts an embodiment of a calibration target that can be configured for use with the assemblies of FIGS. 2(h)-2(k)
Figure 4C:
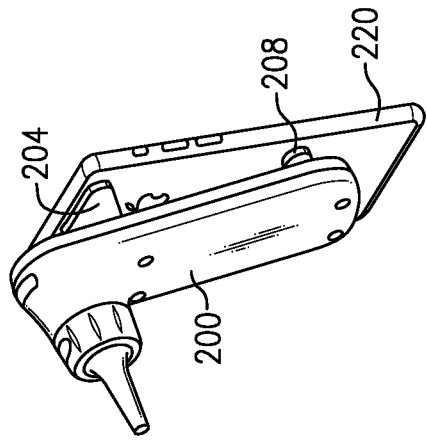
FIG. 4(c) depicts the side perspective view of the medical instrument assembly of FIGS. 4(a) and 4(b) in a nearly assembled condition.
Figure 4F:
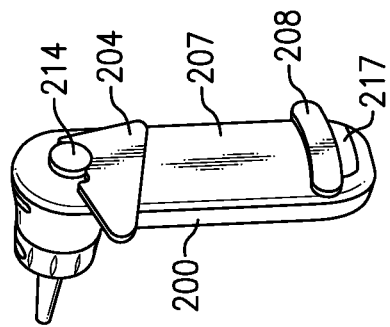
FIG. 4(f) illustrates a rear perspective view of the stand-alone medical diagnostic or examination device of FIGS. 4(a)-4(d) having interface plates attached thereto.
Figure 4B:
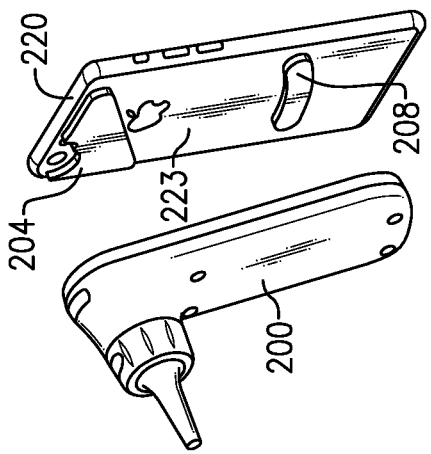
FIG. 4(b) depicts a side perspective view of the medical instrument assembly of FIG. 4(a), with the interface plates as attached to the smart device.
Figure 4E:
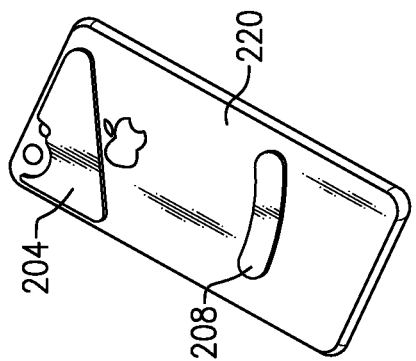
FIG. 4(e) illustrates a front perspective view of the smart device of FIG. 4(d) having the interface plates attached thereto.
Figure 4A:
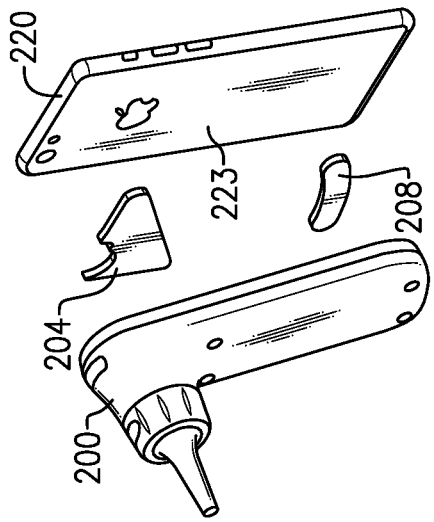
FIG. 4(a) depicts an exploded perspective view of a medical instrument assembly in accordance with another embodiment including a stand-alone medical diagnostic or examination device and various interface plates for use in enabling the aligned attachment of a smart device.
Figure 4D:
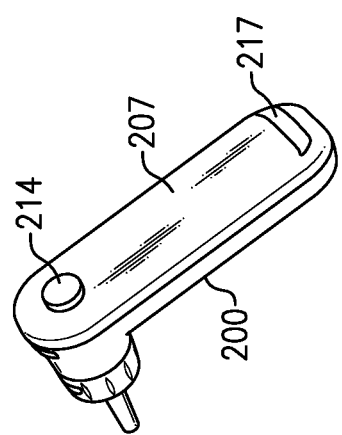
FIG. 4(d) illustrates a rear perspective view of the stand-alone medical diagnostic or examination device of FIGS. 4(a)-4(c), including magnetic areas configured for alignment with a smart device.

When attached in the manner shown herein, the optical parameters of the entire assembly can be calibrated using a calibration target 198, such as shown in FIG. 3 using the display 144 of the mounted smart phone 140. Optical parameters such as white balance, gray scale and color can be optimized using an application stored within the smart device or other suitable means.

It should be understood that the number and location of interface plates used for alignment to a stand-alone medical device can be suitably varied provided that the interface plate(s) accurately align a mounted smart device and more specifically the contained optics of the attached smart device with the optical system of the medical diagnostic or examination device. One alternative embodiment is shown in FIGS. 4(a)-4(f) in which a pair of interface plates 204, 208, are provided for disposition between the rear facing surface 207 of a stand-alone medical diagnostic or examination device 200, in this instance an otoscope, and the front facing surface 223 of a smart device 220, for example, a smart phone. Initially, a pair of interface plates 204, 208 are attached to the front facing surface 223 of the smart device 220 using an alignment fixture (not shown) that is similar to that previously shown and depicted in FIGS. 2(a)-2(l). Though not shown, the process of assembly is similar in that the alignment fixture includes a raised platform or an upper or top planar surface that further includes a pair of slots that are spaced from one another and configured for retaining each of the interface plates in a spaced relation. According to this embodiment, the pair of interface plates include a first interface plate 204 and a second interface plate 208. Also and as in the proceeding, an optical target can be provided on the alignment fixture.

To assemble, each of the first and second interface plates 204, 208 are placed within the retaining slots on the top surface of the alignment fixture with the camera of the smart device 220 being aimed at the optical target and viewed using a cross hair or similar aiming means provided on the display of the smart device 220 using an application stored within the smart device 220. When the camera of the smart device 220 is properly aimed such that the optical target is centered on the cross hairs provided on the display, the smart device 220 can then be brought into contact with the top surface of the alignment fixture in which each of the facing sides of the interface plates 204 and 208 include an exposed adhesive layer in order to secure same to the smart device 220.

The smart device 220 can then be removed from the alignment fixture and secured to the rear facing side or surface 207 of the medical examination device 200, which according to this embodiment is an otoscope. In at least one version, the rear facing side 207 of the medical examination device 200 includes a pair of magnets 214, 217 spaced from one another that receive the smart device 220 and more specifically the interface plates 204, 208, the latter being positioned to ensure the attached smart device 220, and more specifically the camera of the smart device 220, is aligned properly with the optical system of the examination device 200.

With reference to FIGS. 5(a)-5(d), there are depicted a number of varied arrangements between a stand-alone medical diagnostic or examination device 300, an eyepiece 320 and a smart device 360, each of the latter being interchangeably attached to the proximal end of the medical diagnostic device 300.

First and as shown in FIGS. 5(a) and 5(b), the eyepiece 320 can be releasably engaged with the stand-alone medical examination device 300 (i.e., an otoscope). The eyepiece 320 according to this depicted embodiment is defined by a substantially cylindrical housing 324 having an interior that is configured to retain at least one optical element, such as an objective lens (not shown). The eyepiece 320 can be releasably attached to the stand-alone medical examination device 300 by means of a magnetic interface 309 formed at the proximal end of the medical device 300. According to this embodiment, the magnetic interface 309 includes a plurality of retained magnets which are disposed in a circumferential configuration about a proximal opening of the medical device 300. The distal end of the eyepiece 320 is configured to engage the magnetic interface 309 in a manner in which the contained optics of the eyepiece 320 are optically aligned with the contained optics of the medical examination device 300.

The eyepiece 320, according to this specific embodiment, further includes an external focusing knob 328 disposed on the housing 324, that when rotated, is configured to axially shift the position of the contained optical element, as needed. When coupled to the stand-alone medical device 300, the external focusing knob 328 can be accessed by the user and rotated to permit adjustments to be made optically while the magnetic interface 309 continues to maintain support and optical alignment of the eyepiece 320 with the optics of the stand-alone medical device 300.

As shown in FIGS. 6(a) and 6(b), a similar arrangement can be provided for another stand-alone medical diagnostic or examination device 400 (e.g., an ophthalmoscope) in which the eyepiece 320 can also be releasably and interchangeably attached to the proximal end 405 of the device 400. As in the prior embodiment, the device 400 includes a magnetic interface 409 in which a plurality of retained magnets are disposed in a circumferential pattern to enable optical alignment with the stand-alone medical examination device, when the eyepiece 320 is attached. This attachment further enables a user to view the intended target through the proximal end of the eyepiece 320. In use, the eyepiece 320 can be interchangeably attached to either medical diagnostic or examination device 300, 400 without modifications being required to either the devices 300, 400 or the eyepiece 320.

Still further and with reference to FIGS. 5(c) and 5(d), and FIGS. 6(c) and 6(d), a smart device 360 can also be separably and interchangeably attachable to the proximal surface 305, 405 of either medical examination or diagnostic device (otoscope 300 or ophthalmoscope 400) in lieu of the eyepiece 320 to provide a separate electronic imaging or viewing mode. According to each of these depicted embodiments, at least one interface plate is first provided and attached to the front or distal facing side of the smart device 360 such as using an alignment fixture (not shown) in a manner previously described—see FIGS. 2(a)-2(i). Once the interface plate(s) are attached, the smart device 360 can be interchangeably attached to the rear facing or proximal surface 305, 405 of either medical examination device 300, 400 using at least a portion of the magnetic interface 309, 409 as well as at least one other suitably spaced magnet 311, 411, the latter being separately provided on the rear facing surface 305, 405 of the otoscope 300 or ophthalmoscope 400 in spaced relation to the interface 309, 409 to properly locate the smart device 360 in alignment with the contained optics of the medical examination device 300, 400. It should be understood that other configurations are possible.

It should be noted that the design of the medical examination device can be suitably altered to better accommodate an attached and optically aligned smart device for purposes of operation. For example and according to FIGS. 7(a)-7(d) and FIGS. 8(a)-8(d), another embodiment of a medical examination assembly is depicted in which stand-alone medical examination devices (otoscope 500 or ophthalmoscope 600) are commonly defined by a body or housing 504, 604 in which the upper portion of the handle 508, 608 is curved so as to create an offset of the instrument head 510, 610 relative to the handle 508, 608 of the device 500, 600 to enable an attached smart device 360 to be more efficiently centered and balanced due to the off-center nature of an attached smart device 360. Other suitable variations and configurations will be readily evident, for example, depending on the smart device to be supported in the herein described assembly.

In each of the latter examples, an eyepiece 320 and a smart device 360 can be interchangeably used in connection with either medical examination device 500, 600. The eyepiece 320 is releasably attached by engagement of the distal end of the eyepiece housing 324 with a magnetic interface 509, 609 formed about the periphery of the proximal optics opening of the device 500, 600. The smart device 360 is interchangeably mounted using at least one interface plate (not shown in these views) using a technique that is similar to that described in FIGS. 2(a)-2(l), including a suitable alignment fixture having retention slots that permit specific placement or positioning of the smart device 360 to further provide suitable optical alignment relative to an optical target on the alignment fixture that is configured to represent the optical system of the otoscope 500 or ophthalmoscope 600 and attached to magnets 511, 611 of the medical devices 500, 600 respectively.

Figure 9A:
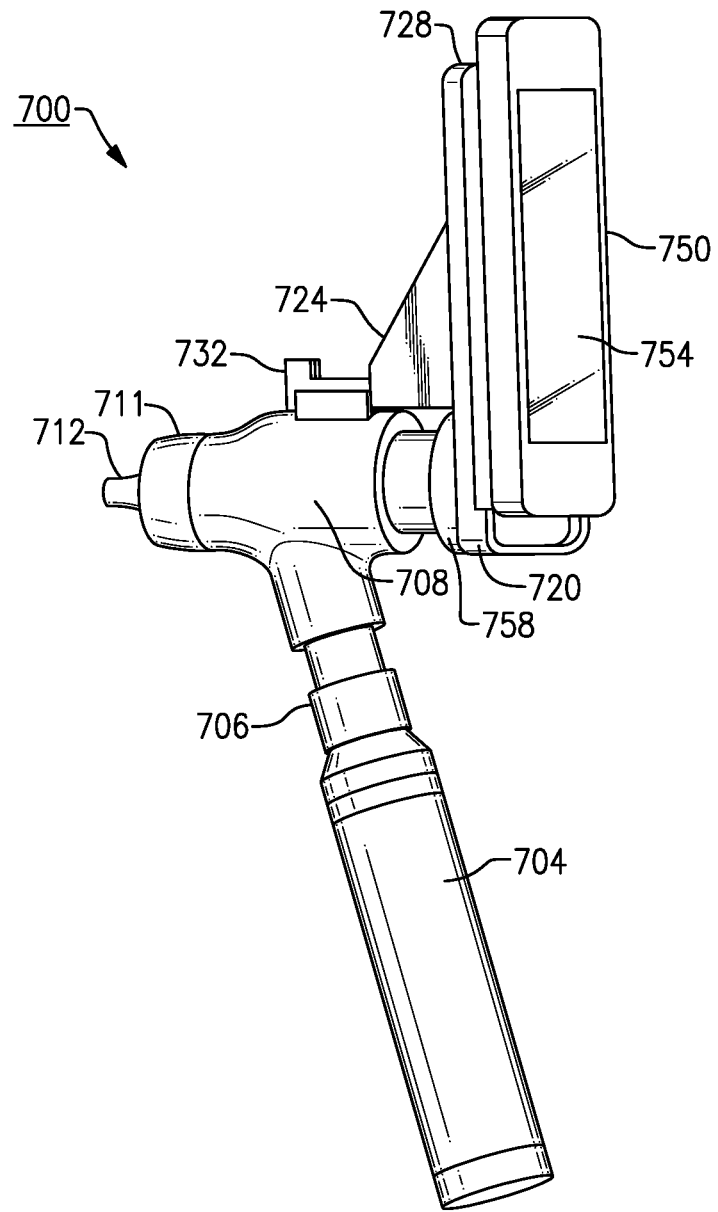
FIG. 9(a) is a side perspective view of a stand-alone medical diagnostic or examination device configured to support an aligned smart device using an adapter in accordance with an embodiment.
Figure 9B:
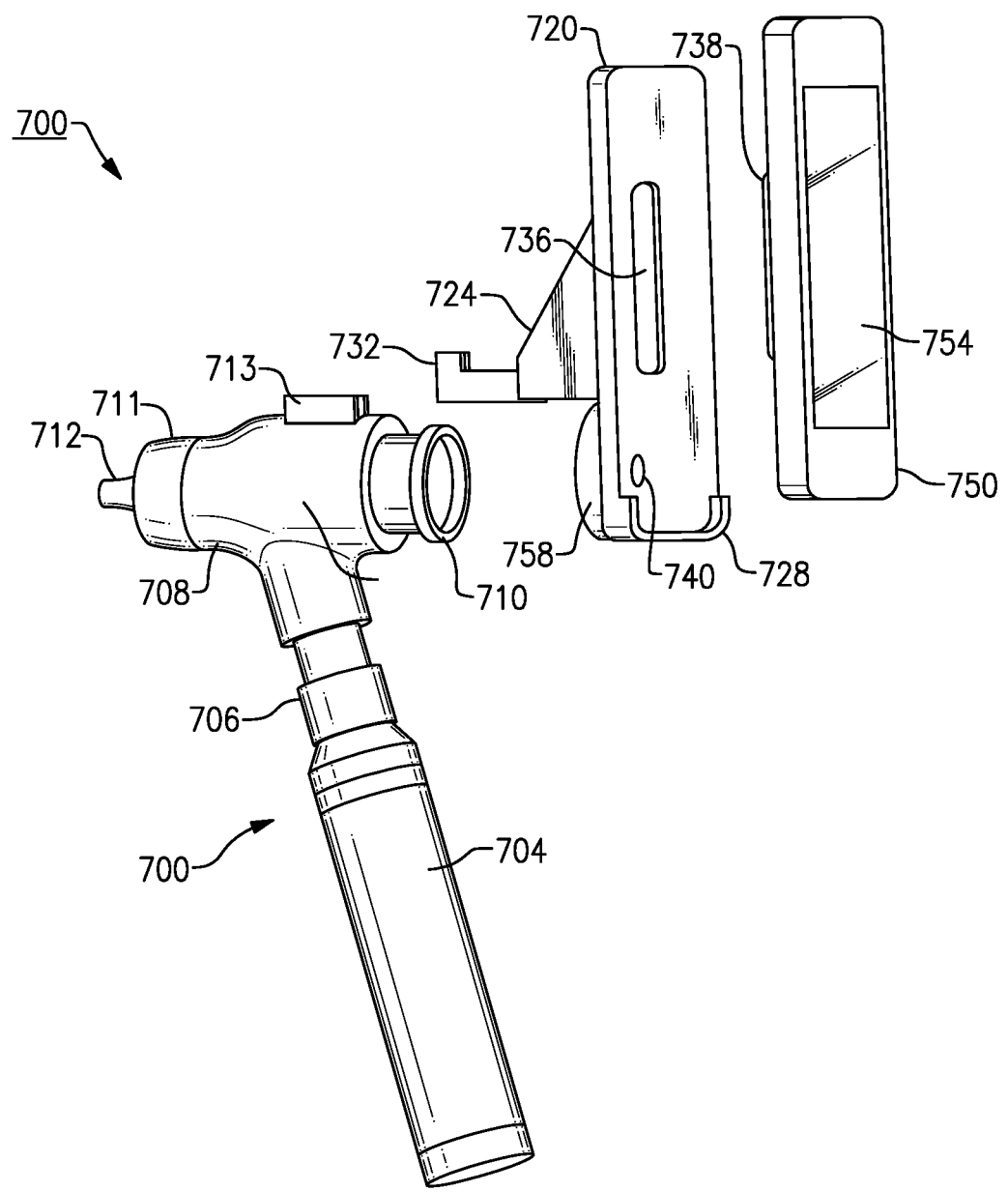
FIG. 9(b) is an exploded assembly view of the medical diagnostic or examination device, adapter and smart device of FIG. 9(a)

In accordance with another embodiment and with reference to FIGS. 9(a) and 9(b) there is shown another stand-alone medical diagnostic or examination device that can be configured to support a smart device to provide versatility through an enhanced electronic viewing mode According to this version, the medical examination or examination device is an otoscope 700, such as the Macroview otoscope manufactured and sold by Welch Allyn, Inc. of Skaneateles Falls, N.Y. This device is described more completely in U.S. Pat. No. 7,399,275, the entire contents of which are herein incorporated by reference. The otoscope 700 according to this embodiment includes a cylindrical handle portion 704 having an upper necked portion 706 that supports an instrument head 708. The handle portion 704 includes a battery compartment (not shown) that retains a set of stacked batteries (not shown) that are coupled to a light source (not shown) retained in the necked portion 706. Light is transmitted from the contained light source through a distal end 711 of the instrument head 708, using a fiberoptic bundle or other suitable means. The fiberoptic bundle (not shown) is configured as a ringlet of fibers that surround a distal optical element (not shown) contained within the instrument head 708. The interior of the instrument head 708 is essentially hollow and includes a conical insertion portion 712 at the distal end 711, as well as a proximal opening including a proximally extending eyepiece 710. In use, an otoscopic tip element (a speculum tip) is releasably attached to a conical insertion portion 712 of the instrument head 708 in which the target of interest (e.g., the tympanic membrane) can be viewed through contained optics via the proximal opening along a defined optical axis. As noted, further details relating to the construction and features of the otoscopic device 700, including the speculum tip, are discussed in greater detail in U.S. Pat. No. 7,399,275, herein previously incorporated by reference.

As further shown in FIGS. 9(a) and 9(b), an adapter 720 is provided that is attached to the proximal end of the otoscopic device 600. According to this embodiment, the adapter 720 is defined by a distal engaging portion 724 that is configured for engaging the instrument head 708 of the otoscope 700 and a proximal supporting portion 728 that is configured to receive a smart device 750, such as a smart phone, as shown. The distal engaging portion 724, according to this specific embodiment, is defined by a pair of resilient fingers 732 that are configured to engage a slot or slotted portion 713 formed on an upper or top surface of the instrument head 708. The proximal supporting portion 728 of the adapter 720 includes a recessed slot 736 sized for receiving an interface plate 738 (partially shown in the exploded view of FIG. 9(b)) that is first attached to the distal facing side or surface of the smart device 750, using an alignment and indexing fixture in a manner similar to that previously described with regard to FIGS. 2(a)-2(l). In this specific version, the slot 736 (or other part of the adapter 720) is further defined by at least one magnet, the adapter 720 further having a through opening 740 that aligns the optics of the device 700 and those of the optics of the smart device 750 opposite a connector 758 at the lower portion of the adapter 720. The connector 758 is configured to engage with and cover the eyepiece 710 of the otoscope 700.

When attached, the smart device 750, including the display 754, is situated substantially above the instrument 700 as is depicted in FIG. 9(a) with the optics of the smart device 750 being disposed in proper alignment with the optical system of the otoscope 700.

Figure 9C:
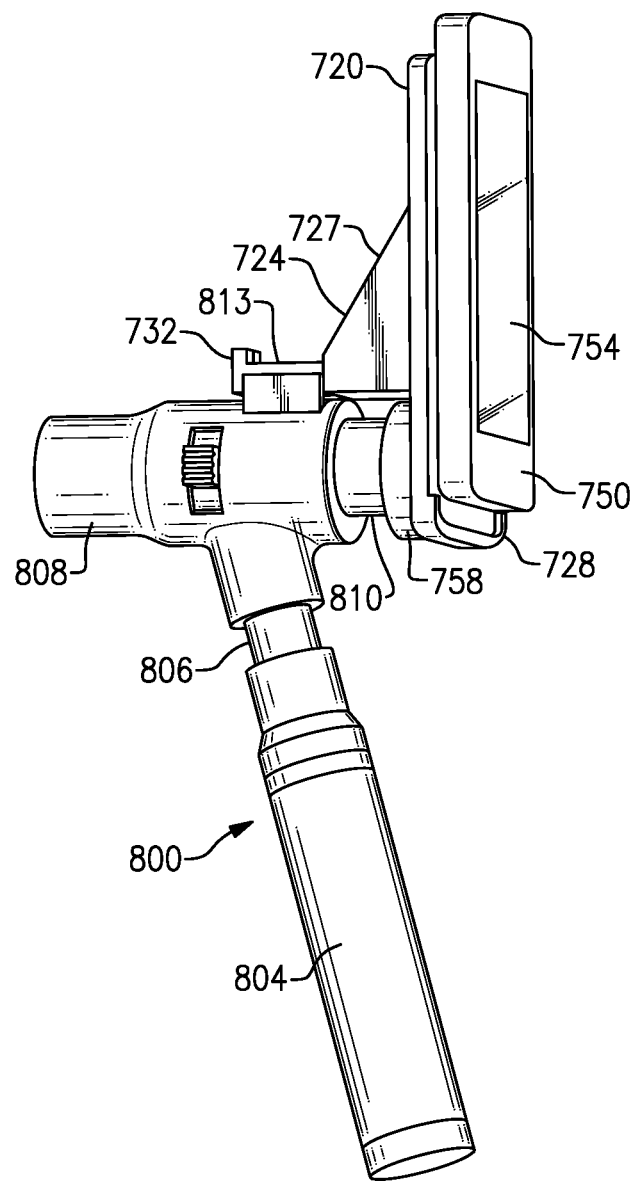
FIG. 9(c) is a side perspective view of another stand-alone medical diagnostic or examination device as configured to support an aligned smart device using an adapter.

The above described adapter 720 can be utilized with other stand-alone medical diagnostic or examination devices. For the sake of clarity, similar parts are herein labeled with the same reference numbers. With reference to FIG. 9(c), an ophthalmoscope 800 includes a handle portion 804 that further includes a necked portion 806 for supporting an instrument head 808. The instrument head 808 retains a plurality of components to enable viewing of a patient's eye (not shown) and more specifically the retina (not shown). According to this embodiment, the device 800 is configured to with an eyepiece 810 at the proximal end of the instrument head 808 in which the interior of the instrument head 808 includes a plurality of optical elements as well as an illumination system, the latter having a contained light source for viewing portions of the eye of the patient. Details relating to the salient features of the ophthalmoscope 800 are provided in U.S. Pat. No. 6,065,837, the entire contents of which are herein incorporated by reference.

The adapter 720 is attached to the instrument 800 to permit interchangeability between instruments and operating modes (between an optical viewing mode using the eyepiece 810 and an electronic viewing mode using an attached smart device 750). As previously discussed, the adapter 720 includes a distal engaging portion 724 and a proximal supporting portion 728. The distal engaging portion 724 includes a pair of resilient fingers 732 that are configured to engage a recessed slot or slotted portion 813 provided in an upper surface of the instrument head 808. The proximal supporting portion 728 is defined by a vertical support surface including a recessed slot (not shown) that receives an interface plate attached, adhesively or otherwise, to the distal or front facing side of the smart device 750 preferably in the manner previously described. The adapter 720 further includes a cylindrically shaped connector portion 758 in a lower portion of the adapter 720 that is sized to engage the eyepiece 810 of the ophthalmoscope 800 or other medical stand-alone device and in which a gusset 727 engages a top portion of the instrument head 808 to optionally provide additional support and stability.

Figure 9D:
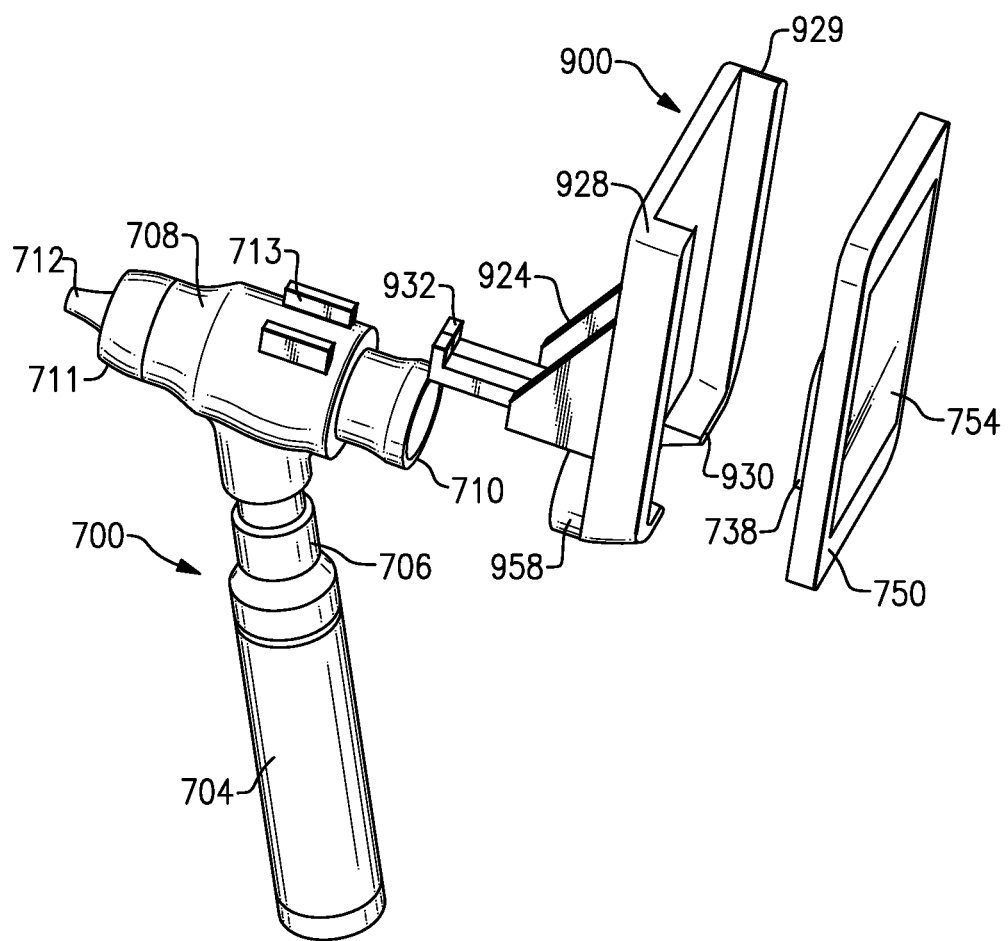
FIG. 9(d) is an exploded assembly view of the stand-alone medical diagnostic or examination device and smart device of FIGS. 9(a) and 9(b) and an adapter made in accordance with another embodiment.

With reference to FIG. 9(d), an alternative adapter is depicted for use with a stand-alone medical diagnostic or examination device (e.g., the otoscope 700 previously discussed). According to this version, the adapter 920 includes a proximal supporting portion 928 that includes an open end 929 and a pair of laterally disposed guide rails 930, the latter being sized to receive a smart device 750. According to this specific embodiment, the adapter 920 includes a distal engaging portion 924 having a set of resilient fingers 932 that are configured to engage the slotted portion 713 formed on the upper or top surface of the instrument head 708. The adapter 920 also includes a lower connector portion 758 that is sized to engage the eyepiece 710 of the diagnostic or examination device 700. Each of the herein described adapters 720, 920 enable a smart device, such as device 750, to be attached to at least one stand-alone medical instrument and permit interchangeable operating modes (optical and electronic).

Yet another embodiment of a medical instrument assembly or system is illustrated in FIGS. 10(a)-10(b). According to this version, a stand-alone medical examination or diagnostic device (e.g., an otoscope 1000) is provided that is defined by a housing 1004 further defined by a handle 1008 that downwardly extends from an instrument head 1010. The instrument head 1010 is defined by a distal end 1012 including a conically shaped insertion portion (not shown). The insertion portion is configured to releasably support a conically shaped and hollow speculum tip element 1014, the tip element 1014 being releasably attached by means of a rotatable actuator knob 1015. Alternatively, the tip element 1014 can be secured by manually twisting the element in place onto the conical insertion portion using bayonet or other suitable engagement features. Details relating to the speculum tip element and an exemplary attaching and releasing mechanism are described in greater detail in U.S. Pat. Nos. 7,354,399 and 8,197,403, each of which are herein incorporated by reference in their entirety.

Within the interior of the otoscope 1000 is a light source (not shown) such as an incandescent lamp or at least one LED, which is disposed in a lower portion of the instrument head 1010. A bundle of optical fibers (not shown) are coupled to the light source and directed as a ringlet at the distal end of the conical insertion portion in order to effectively illuminate the target of interest. The handle 1008 includes an interior compartment that retains at least one battery (not shown) for energizing the light source. A series of optical elements are disposed within the interior of the instrument head 1010 and aligned along an optical axis with a separate optical train being provided within the confines of an eyepiece 1024, the latter being releasably attached to the otoscope 1000 in order to create an optical viewing mode.

According to this embodiment an adapter 1020, which is provided at a proximal end of the otoscope 1000, permits attachment of the eyepiece 1024. The adapter 1020 includes a set of magnets (not shown) that permits releasable and interchangeable attachment of the eyepiece 1024 or a smart device 1050, as described below. As noted, the eyepiece 1024 includes an interior retaining a series of optical elements that are suitably aligned with optical elements provided in the interior of the instrument head 1010. According to this specific embodiment, the eyepiece 1024 is defined by a housing 1027 that is coextensive with the handle 1008 of the otoscope 1000, including a substantially planar distal facing surface 1029.

With further reference to FIG. 10(a), the adapter 1020 is attached to or according to this embodiment is directly integrated as a part of the device housing 1004. More specifically, the adapter 1020 is defined by a planar section 1022 which is disposed within a rear receiving slot 1036 of the device housing 1004. This planar section 1022 includes a proximal face surface 1026 having at least one recessed slot (not shown) that permits the selective engagement of a smart device 1050, FIG. 10(b). In accordance with prior embodiments discussed, such as depicted in FIGS. 2(a)-2(l), an attachment device includes at least one retaining slot that receives an interface plate. The smart device 1050 is then positioned in relation to the alignment fixture and the camera of the smart device 1050 is aimed at an optical target of the alignment fixture until centered in the display of the smart device 1050. Upon centering and as previously discussed, the smart device 1050 is then engaged with the supported interface plate(s), the latter having an adhesive layer to provide securement. The indexing and positioning of the interface plate(s) guarantees proper alignment of the smart device 1050 to the otoscope 1000 and more specifically between the interface plate(s) and the at least one recessed slot (not shown) formed in the proximal facing surface 1026 of the adapter 1020. The at least one magnet (not shown) is provided in the adapter 1020 in alignment with the recessed slot(s) to releasably secure the smart device 1050.

According to this embodiment, the adapter 1020 is supported for pivotal movement from the rear receiving slot 1036 of the device housing 1004 about the optical axis of the device 1000. This pivotability permits the attached smart device 1050 to assume a plurality of adjustable mounting orientations enabling the position of the smart device 1050 to be changed selectively. Advantageously, this latter feature permits enhanced operation and versatility.

In terms of operation, the herein described system can be used initially in an optical viewing mode as depicted in FIG. 10(a) with the eyepiece 1024 being releasably engaged with the proximal facing surface 1026 of the adapter 1020. The eyepiece 1024 is releasably attached and can be released from the adapter 1020 by disrupting the magnetic attachment. As shown in FIG. 10(b), the smart device 1050, having an attached interface plate(s) (not shown) can then be interchangeably attached in lieu of the eyepiece 1024 by engaging the interface plate with the recessed receiving slot of the adapter 1020. The magnets according to this embodiment are directly aligned with the recessed receiving slot on the adapter 1020 to insure attachment. In this latter mode, the camera of the smart device 1050 is aligned with the optical axis of the otoscope 1000 and the smart device 1050 is further configured to assume a plurality of mounting configurations based on the pivotal connection of the adapter 1020 with the remainder of the otoscope 1000.

In either operational mode, the user inserts the speculum tip element 1014 a predetermined distance into the outer ear of a patient and the image of the intended target, as illuminated by the contained light source is viewed or transmitted directly along the optical axis to either the eyepiece 1024 or the smart device 1050 for viewing on the display 1054, FIG. 10(b).

Figure 11B:
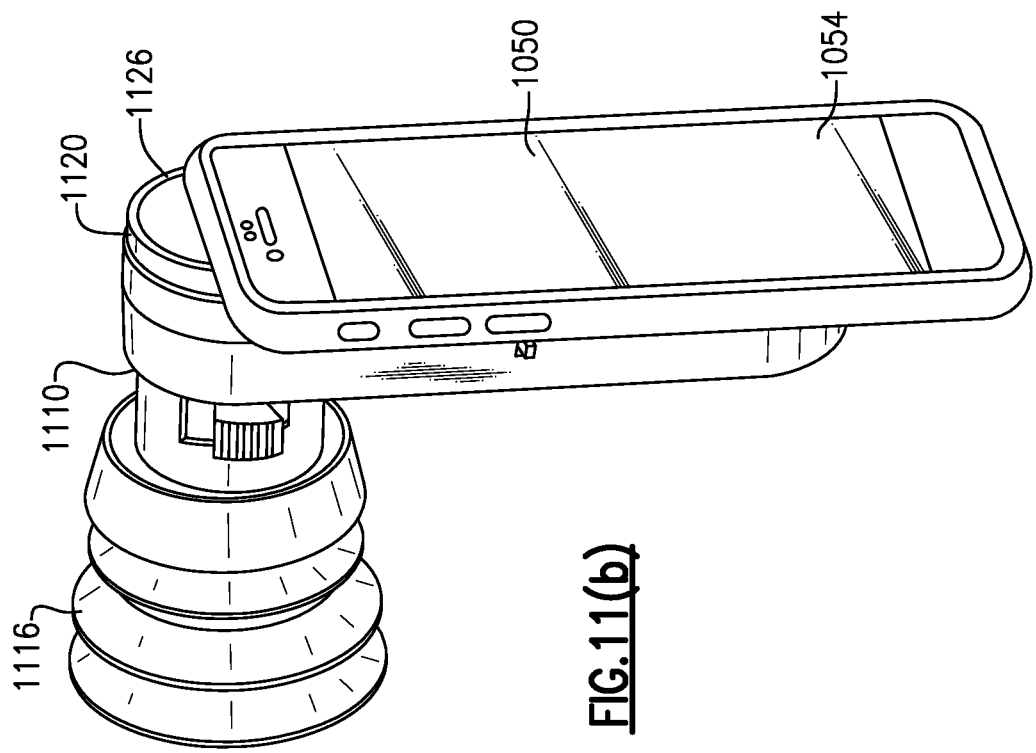
FIG. 11(b) is a perspective view of the medical examination device of FIG. 11(a), including an attached smart device, the medical examination device being configured in an electronic viewing mode.
Figure 11A:
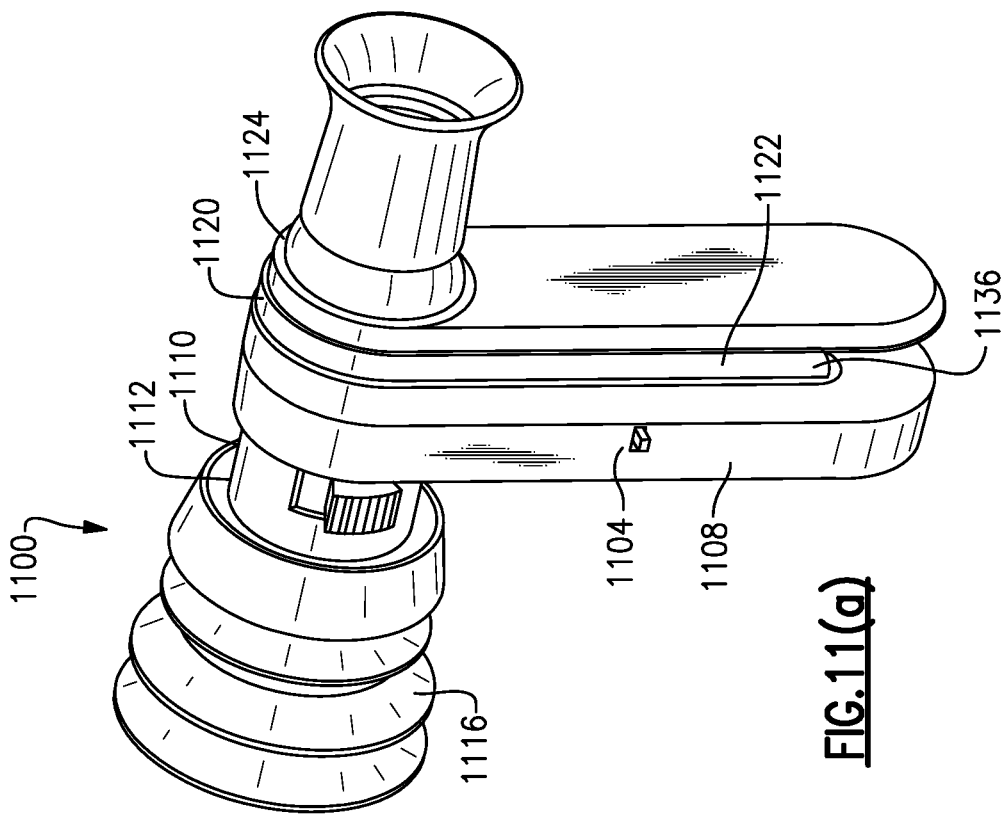
FIG. 11(a) is a perspective view of a medical examination device made in accordance with another embodiment in which the device is configured in an optical viewing mode.

Another medical examination system is depicted in FIGS. 11(a)-11(b). According to this embodiment, the medical diagnostic or examination device used is an ophthalmoscope 1100 defined by a housing 1104 having a handle portion 1108 and an instrument head 1110. The instrument head 1110 is defined by a distal end 1112 that receives an elastomeric eye cup 1116 configured to engage against the patient and a proximal end that includes an adapter 1120. The interior of the instrument head 1110 includes an optical and illumination system that is configured to view the eye (e.g., the retina) of a patient (not shown) including a defined optical axis extending between the distal and proximal ends of the device 1100. The adapter 1120, which is similar to that previously described in the prior embodiment, is configured to interchangeably receive either an eyepiece 1124, FIG. 11(a), or a smart device 1050, FIG. 11(b), respectively.

As in the prior otoscopic version, the adapter 1120 is defined by a planar section 1122 which is disposed within a rear receiving slot of the device housing 1104. This planar section 1122 includes a proximal or rear face surface 1126 having at least one recessed slot (not shown) that permits the selective engagement of a smart device 1050. In accordance with prior embodiments discussed, such as depicted in FIGS. 2(a)-2(l), an alignment fixture includes at least one retaining slot that receives an interface plate. The smart device 1050 is then positioned in relation to the alignment fixture and the camera of the smart device is aimed at an optical target of the alignment fixture until centered in the display of the smart device. Upon centering and as previously discussed, the smart device is then engaged with the supported interface plate(s), the latter having an adhesive layer to provide securement. The indexing and positioning of the interface plate(s) guarantees proper alignment of the smart device 1050 to the ophthalmoscope 1100 and more specifically between the interface plate(s) and the at least one recessed slot formed in the rear facing surface 1126 of the adapter 1120. At least one magnet (not shown) is provided in the adapter 1120 in alignment with the recessed slot(s) to releasably secure the smart device 1050.

According to this embodiment, the adapter 1120 is supported for pivotal movement from the rear receiving slot 1136 of the device housing 1104 about the optical axis of the device 1100. The adapter 1120 includes a distal engagement portion (not shown) that is disposed over a proximally extending end (not shown) of the instrument head 1110 in overlaying relation. This pivotability feature permits the attached smart device 1050 to assume a plurality of adjustable mounting orientations about the optical axis wherein the position of the smart device 1050 can be changed selectively upon attachment to the adapter 1120 without otherwise disturbing optical alignment. For example, the engagement portion can include at least one or more detents (not shown) to provide specific mounting orientations (e.g., each 90 degrees to create four (4) mounting orientations). Advantageously, this latter feature permits enhanced operation and versatility.

Figure 12B:
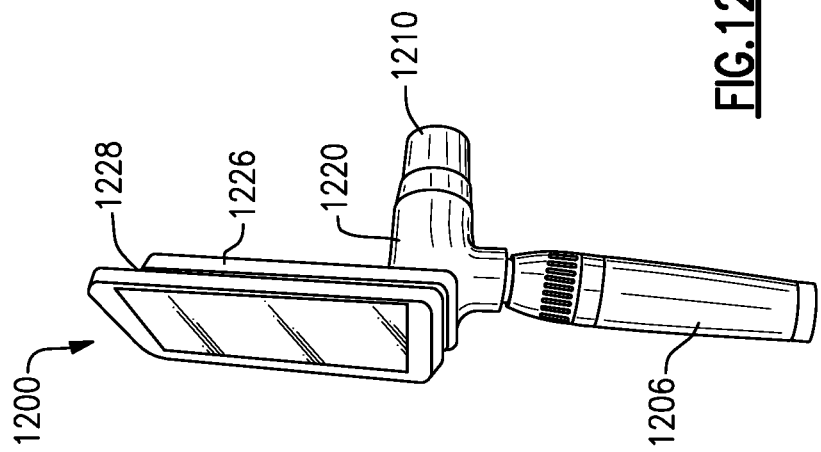
FIG. 12(b) is another perspective view of the medical diagnostic or examination instrument of FIG. 12(a), with the attached smart device in another adjustable mounting orientation.
Figure 12A:
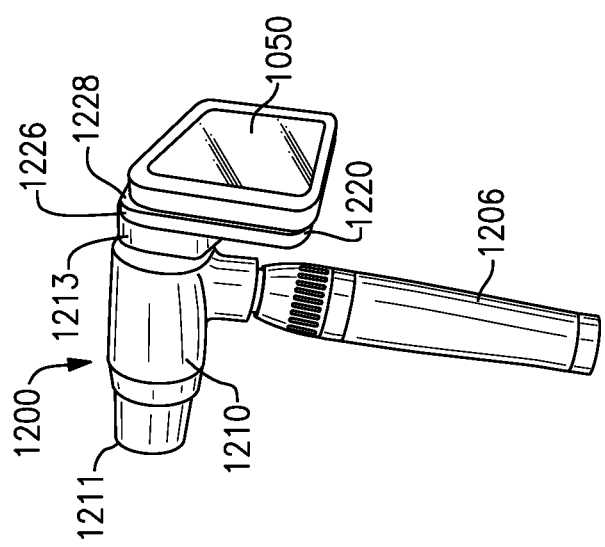
FIG. 12(a) is a perspective view of another medical diagnostic or examination device having a smart device attached thereto in accordance with another embodiment, the smart device being disposed in a specific adjustable mounting orientation.

With reference to FIGS. 12(*a*) and 12(*b*), there is shown another embodiment of a medical examination system that permits pivotal movement of an attached smart device. This system includes a medical examination device (i.e., an ophthalmoscope 1200) having a cylindrical handle portion 1206 with an instrument head 1210 attached to an upper part of the handle portion 1206. The instrument head 1210 is defined by a distal end 1211 and an opposing proximal end 1213, the distal and proximal ends 1211, 1213 defining an aligned optical axis of the assembly. The adapter 1220, according to this embodiment, is defined by a substantially planar section having a distal facing surface 1226 and a proximal facing surface 1228. The proximal facing surface 1228 includes at least one recessed slot (not shown) that is configured for receiving an interface plate (not shown) attached to the front facing side of a smart device 1050, in a manner as previously described. According to this embodiment, the distal facing surface 1226 of the adapter 1220 includes at least one magnet directly aligned with the recessed slot, as well as a distal engagement portion including an open upper end and a channel that is configured to receive an eyepiece portion of the instrument head 1210. The eyepiece portion according to this embodiment includes a necked portion including a proximal lip that axially secures the adapter 1220 once attached to the device 1200.

Figure 13A:
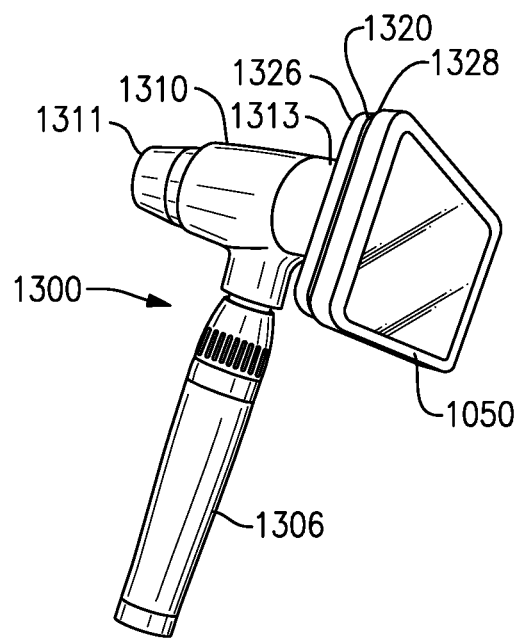
FIG. 13(a) is a perspective view of another medical diagnostic or examination device having a smart device attached thereto in accordance with yet another embodiment, the smart device being disposed in a specific adjustable mounting orientation.
Figure 13B:
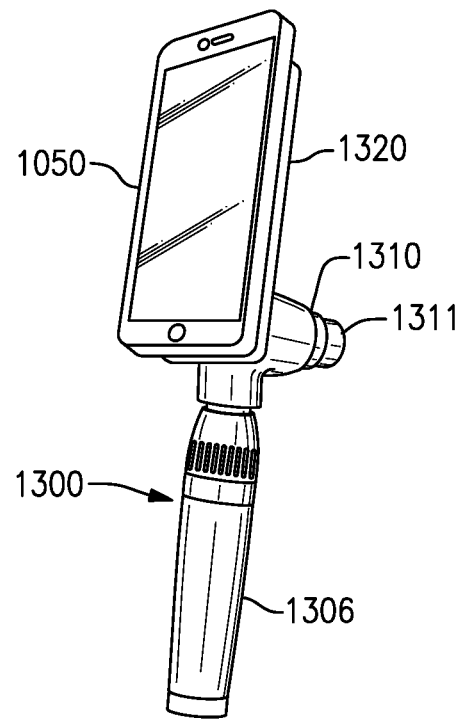
FIG. 13(b) is the perspective view of the medical diagnostic or examination instrument of FIG. 13(a), the attached smart device being disposed in another adjustable mounting orientation.

When attached, the necked portion can be slidingly engaged within the defined channel with the proximal lip being retained within the channel. In at least one variation, the channel and the proximal lip are configured to permit the adapter (and attached smart device) to assume a plurality of mounting orientations, such as shown in FIGS. 12(*a*) and 12(*b*), as well as FIGS. 13(*a*) and 13(*b*) depicting another stand-alone medical device, i.e., an otoscope 1300 having a handle portion 1306 downwardly extending from an instrument head 1310 having respective distal and proximal ends 1311, 1313. As in the preceding, the otoscope 1300 can be similarly configured with the same or similarly configured adapter 1320 that permits the further attachment of a smart device that, upon attachment, can be oriented in various orientations based on a pivotal connection between the medical device and the adapter. As in the preceding, the adapter 1320 is a planar section having a distal facing surface 1326, a proximal facing surface 1328 and a distal engagement portion (not shown) that is sized to overlay the proximal eyepiece end of the instrument head 1310.

Figure 14A:
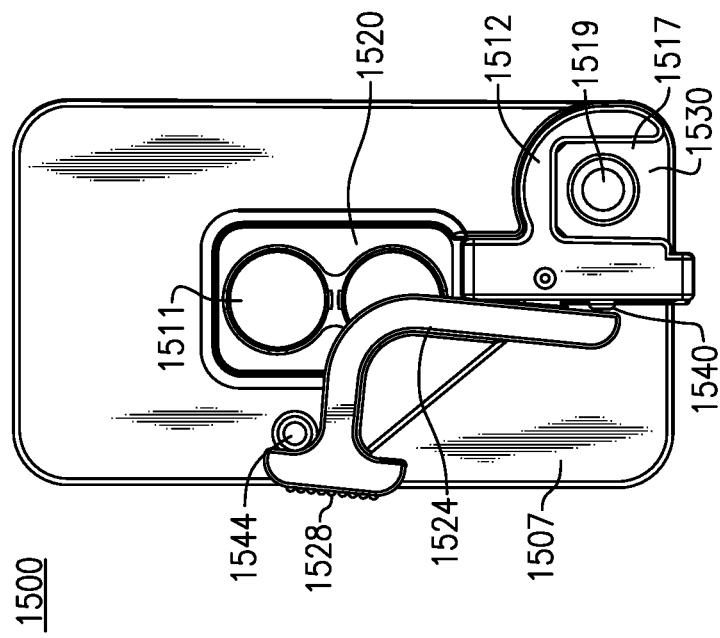
FIG. 14(a) is a front facing view of an adapter made in accordance with another embodiment.
Figure 14B:
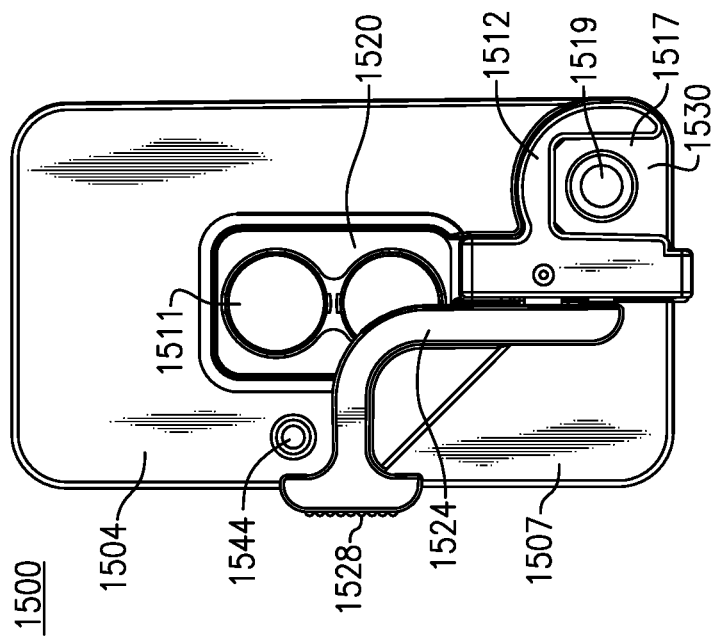
FIG. 14(b) is an end view of the adapter of FIG. 14(a)
Figure 14C:
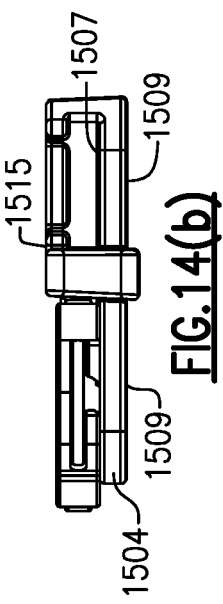
FIG. 14(c) is the front facing view of the adapter of FIGS. 14(a) and 14(b), with a lever moved to a depressed position.

With reference to FIGS. 14(*a*)-15(*c*), an adapter 1500 in accordance with another embodiment is herein described. The adapter 1500 is preferably fabricated from a lightweight structural material, such as a moldable plastic, having a supporting member or body 1504 that includes a forward or front facing side 1507 and a rear facing side 1509, respectively. The adapter 1500 is further configured with a device connection portion 1512 extending from the front facing side 1507 that is configured for attaching the adapter 1500 to a medical examination device. The adapter 1500 is further configured such that a smart device 1550 can be releasably or otherwise attached to the rear facing side 1509 of the supporting member 1504. A center portion 1520 located on the rear facing side 1509 is sized for accommodating an interface plate (not shown) that is attached to the smart device 1550 (e.g., a smart phone). The interface plate can be properly located and positioned on the smart device 1550 by means of a fixture such as shown in FIGS. 2(*a*)-2(*l*) or a similar technique for purposes of aligning the camera of the smart device 1550 with the optical system of the medical examination device, as further discussed herein. A set of magnets 1511 provided in the center portion 1520 releasably secures the smart device 1550 in position on the adapter 1500.

Figure 15C:
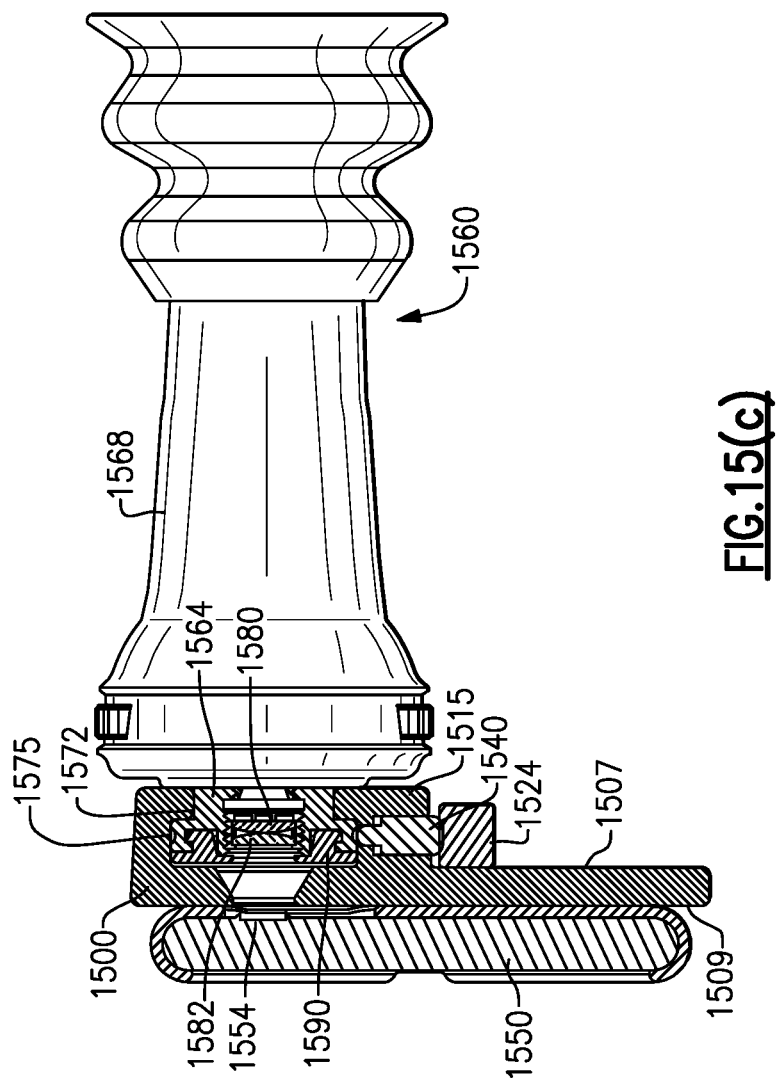
FIG. 15(c) is the side elevational view of medical examination device of FIGS. 15(a) and 15(b), showing the interface between a proximal receiving portion and the adapter shown in section.

According to this embodiment, the device connection portion 1512 is defined by an outer surface 1515 which is parallel to the front facing surface 1507 with a shaped recess 1530 formed between the surfaces 1507, 1515 that is configured for releasable engagement with a proximal receiving portion 1564, FIG. 15(*c*), of a medical examination device 1560, FIG. 15(*c*). A portion of the outer surface 1515 is cutout as shown by 1517, the cutout portion 1517 being aligned with a through opening 1519 formed in the supporting member 1504. One end of a release lever 1524 is disposed in relation to the device attachment portion 1512, wherein the opposite end of the lever 1524 is accessed by a user to move the lever 1524 between undepressed and depressed positions as shown in FIGS. 14(*a*) and 14(*c*), respectively. The end of the release lever 1524 disposed in relation to the device connection portion 1512 is engaged by a spring-loaded pin 1540, partially shown, that is movable into and out of the shaped recess 1530 of the device connection portion 1512. A stop 1544 disposed on the front facing side 1507 of the adapter 1500 provides a limit for movement of the release lever 1524 for the depressed position.

The design of the adapter 1500 enables a plurality of smart devices, such as smart phones, each being different in terms of overall footprint to be releasably attached in a specific orientation. As noted and for locating the smart phone according to this version, an interface plate such as previously described above is placed specifically on the front facing side of the smart device 1550 before releasably securing the smart device 1550 to the rear facing side 1509 of the adapter 1500. When attached in this manner, the camera aperture 1554 of the smart device 1550 is aligned with the through opening 1519 of the adapter 1550.

Referring to FIGS. 15(*a*)-15(*c*), the adapter 1500 is shown as attached to a medical examination device 1560 that includes an instrument head or housing 1568 having a proximal receiving portion 1564. The proximal receiving portion 1564 according to this embodiment is a substantially cylindrical portion that extends rearwardly from the proximal end of the instrument head 1568. The receiving portion 1564 further includes a channel 1572, the latter preferably having a plurality of flats (not shown in this view, but shown as 1430 in a similar medical device shown in FIG. 22(*b*). The formed recess 1530 is aligned so that the adapter 1500 can be slid over the proximal receiving portion 1564 (in a direction into and out of the plane of the drawing). When engaged, the upper surface 1515 engages the channel 1572 and the formed recess 1530 is engaged by an outer ringed portion 1575 of the proximal receiving portion 1564. When engaged, the through opening 1519 of the adapter 1500 is aligned with the optical axis of the medical examination device, including a set of eyepiece lenses 1580, 1582 disposed in the interior of the proximal receiving portion 1564. According to this embodiment, the adapter 1500 can assume one of a plurality of mounting orientations by placing the device connection portion 1512 of the adapter 1500 and more specifically the shaped recess 1530 relative to the proximal end of the medical device 1560.

In operation and when the adapter 1500 is not attached, the medical device 1560 can be used in an optical viewing mode to view the target of interest through the proximal end, which includes a brow rest 1590. The medical device 1560 can be alternatively used in an electronic imaging mode when the adapter 1500 is attached in which the aperture 1554 of the attached smart device 1550 is aligned with regard to the convergence point of the optics of the medical device 1560 such that the smart device 1550 receives a focused image of the medical target of interest. According to this embodiment, the adapter 1500 enables the attachment of one of a plurality of disparate smart devices and in which the attached smart device 1550 is fully aligned with the optical system of the medical device 1560. Each of the above operating modes can be realized without modification to the medical device 1560 by the inclusion or removal of the adapter 1500. That is, no additional optical module is required.

In addition to being configured to receive one of a plurality of different smart devices, the herein described adapter 1500 can be used with a plurality of disparate medical diagnostic instruments, each having a proximal end and receiving portion as described for purposes of attachment. These instruments can include, but are not limited to a ophthalmoscope, an otoscope, a colposcope, a dermatoscope, a rhinoscope, an anoscope or other hand-held medical examination device. For example and in a wellness examination, the adapter 1500 (and attached smart device 1550) can be interchangeably used with an otoscope and an ophthalmoscope for viewing the ears and the eyes, respectively, using the display of the connected smart device 1550. It will be understood, however, that the connective features of this embodiment is an example wherein other suitable configurations are possible for enabling the above-described functions.

With reference to FIGS. 16-19, a number of optical configurations are depicted based on the various operating modes of the herein described examination system and as typified by the preceding structural embodiments. For purposes of this discussion, these schematic diagrams pertain to otoscopes and ophthalmoscopes in keeping with the embodiments previously discussed. It should be understood that other versions could be contemplated.

In certain ophthalmoscopes, optical adjustments can be accomplished in the removable eyepiece of the instrument. For purposes of interchangeability and additional operating modes for the herein described examination system and when a smart device was used in the combination with the ophthalmoscope during tests, it was determined that the device needed a focus range of about +/−10 diopters to accommodate all patients, while the imaging system of known smart devices typically only had a focus range of about +/−3 diopters. Based on the foregoing, it was concluded that there is a need to move the focus adjustment to the patient end (distal) of the instrument to permit focusing in both operational modes of the system; that is either with or without a smart device being attached.

Figure 16:
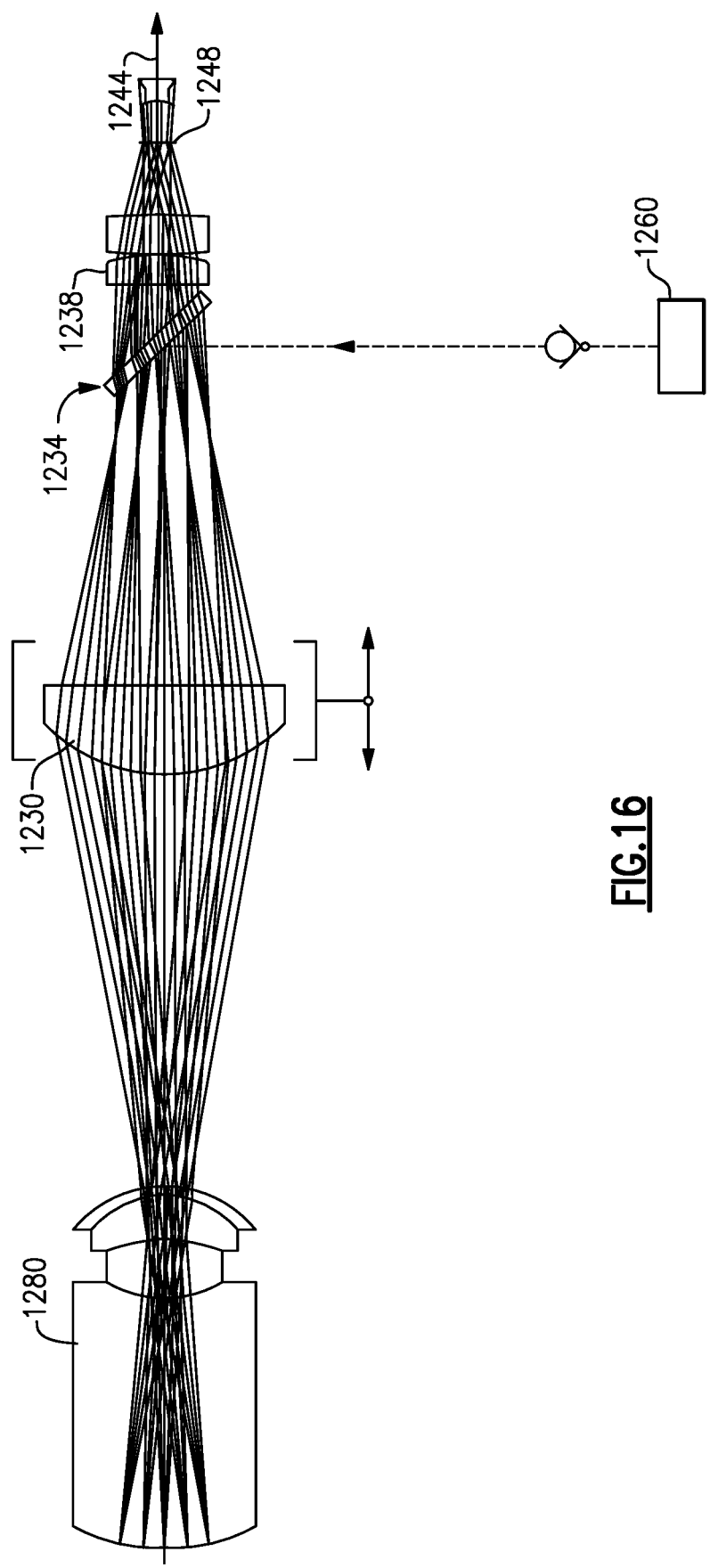
FIG. 16 is a schematic diagram of an optical layout for a stand-alone medical diagnostic or examination device in accordance with an embodiment, the device including an attached smart device and including movable optics provided within the stand-alone medical device.
Figure 17:
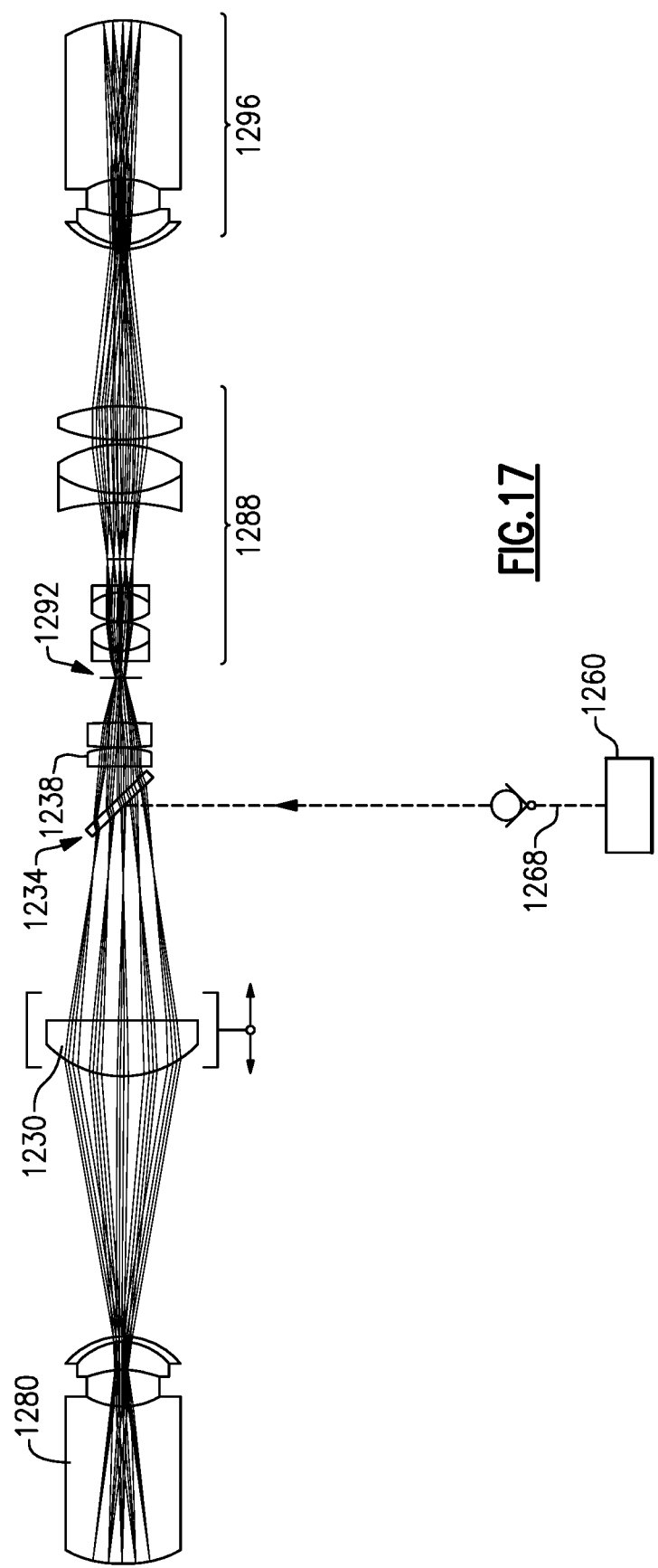
FIG. 17 is a schematic diagram of an optical layout of the stand-alone medical device of FIG. 16, including a coupled eyepiece defining an optical viewing mode.

FIGS. 16 and 17 herein present schematic views of the optical system of the ophthalmoscope 1200 that is configured to provide focusable adjustment of an optical element (objective lens) retained within the instrument head (not shown). First and with reference to FIG. 16, a focusable objective lens 1230 is disposed within the instrument head distally of a beam splitter 1234 and a set of focusing or imaging lenses 1238, each commonly aligned along a defined optical axis 1244. An image sensor 1248 of a smart device attached to the proximal end of the medical device 1200 is also aligned with above optical elements. The beam splitter 1234 is configured to receive illumination from an off-axis light source 1260 such as an LED or an incandescent bulb, the light emitted by this source 1260 being directed to the eye 1280 of a patient (shown schematically) while further permitting reflected light from the patient's eye 1280 to be transmitted and focused at the camera sensor 1248 by the focusing lenses 1238.

By optionally making the objective lens 1230 axially movable according to this embodiment, an increased focus range can be achieved. In this configuration, the autofocus function of the attached smart device should be disabled. The optical system of the instrument 1200 and more specifically the contained objective lens 1230 can be optionally adjustable according to one version using a focusing mechanism, such as a focusing knob (not shown) provided on the instrument head. Details relating to one example of a focusing mechanism for use in a medical examination device is more completely described in U.S. Pat. No. 7,399,275, previously incorporated by reference. The focusable objective lens can according to one embodiment be adjusted +/−20 diopters, or minimally +/−10 diopters.

In lieu of the smart device, an optical layout is presented in FIG. 17 that again includes the objective lens 1230, the beam splitter 1234 and the focusing or imaging lenses 1238 each commonly disposed along the defined optical axis 1244 of the device 1200 extending through the distal and proximal ends of the instrument head along with the aligned optical train of an attached eyepiece, such as shown. In this version, the optical train of the attached eyepiece includes a plurality of fixed eyepiece lenses 1288 and a distal aperture stop 1292, each also aligned along the defined optical axis 1244 for viewing by the eye 1296 of the doctor. As in the previous example, the objective lens 1230 contained within the instrument head is axially movable to increase the focusing range of the device 1200.

Figure 18:
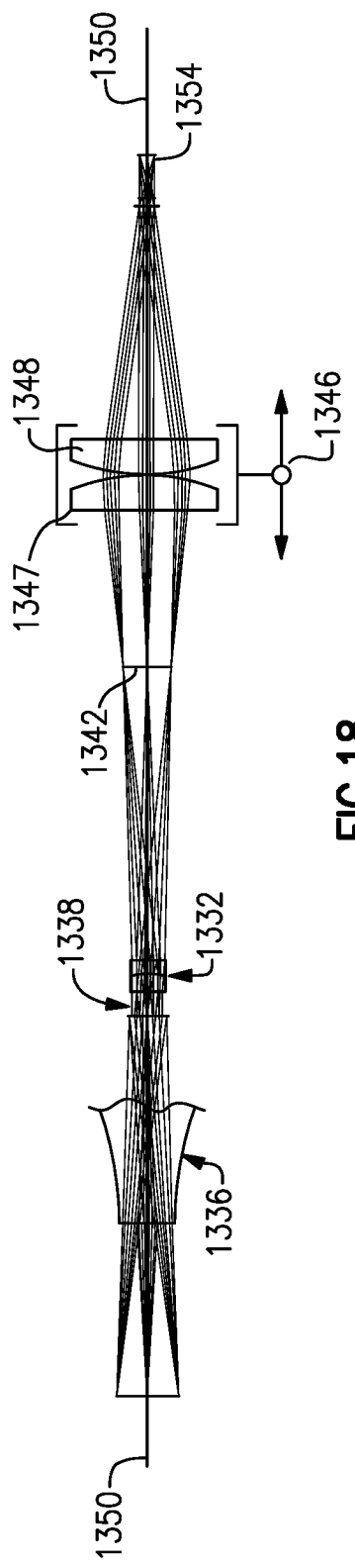
FIG. 18 is a schematic diagram of an optical layout for a stand-alone medical diagnostic or examination device in accordance with another embodiment, the device including movable optics contained in the device and an attached smart device defining an electronic imaging mode.
Figure 19:
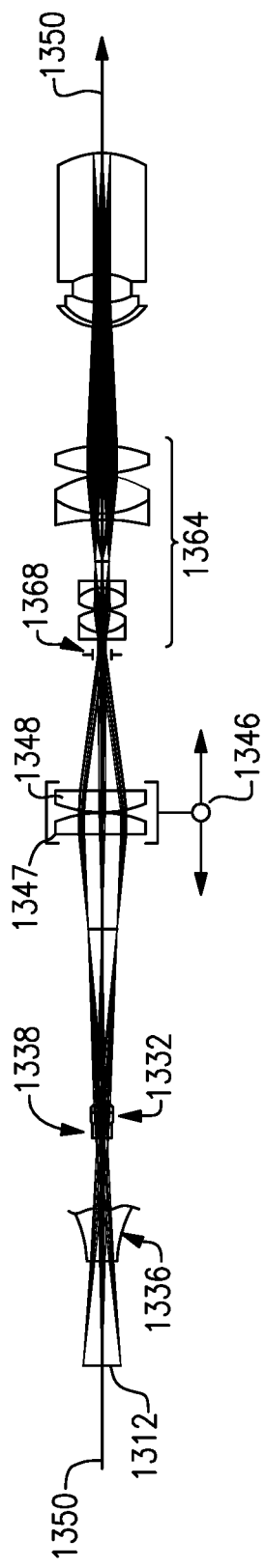
FIG. 19 is a schematic diagram of an optical layout of the stand-alone medical device of FIG. 18, including a coupled eyepiece.

Similar arrangements can be provided in another medical examination or diagnostic device. Referring to FIGS. 18 and 19, imaging and optical (eyepiece) modes are shown schematically for an otoscope 1300 that is defined by a distal lens 1332 disposed in relation to the speculum tip element shown partially as 1336, the latter being releasably attached to the distal end of the instrument head. The distal lens 1332 according to this embodiment is covered by a plano window 1338 wherein a field stop 1342 is provided in relation to a focusable objective lens 1346, which in this version is a doublet defined by a first lens 1347 and a second lens 1348. The first distalmost lens 1347 is defined by a distal plano surface and an opposing concave surface. The second adjacent lens 1348 of this doublet is defined by a distal concave surface and an opposing plano surface. Each of the above optical elements are commonly aligned along a defined optical or imaging axis 1350 extending through the distal and proximal ends with the instrument having an attached speculum tip element 1336, also shown schematically according to these examples. In the version shown in FIG. 18, the system includes an optically aligned smart device, shown diagrammatically as 1354, the device including a camera aperture as well as an image sensor disposed and aligned along the defined optical axis 1350, such as through use of an interface plate and adapter as described with regard to FIGS. 12(*a*)-15(*c*).

As shown in FIG. 19, the otoscope 1300 alternatively receives the attached eyepiece, which includes a set of fixed eyepiece optics 1364 and an aperture stop 1368 that is aligned with the eye of the doctor or caregiver along the defined optical or imaging axis of the assembly. In each depicted version, the focusable objective lens 1346 is disposed adjacent the proximal end of the instrument head (not shown) and aligned with the camera lens and the image sensor of the attached smart device or the eyepiece. A focusing mechanism can also be provided, such as described, by way of example, in previously incorporated U.S. Pat. No. 7,399,275. In terms of operation, an image of the tympanic membrane, shown schematically as 1312, is transmitted through a plano window at the distal end of the conical insertion portion and through an adjacent distal lens through a field stop and then to the focusable objective lens 1346, which condenses the image taken through either the attached eyepiece to the doctor's eye 1362 or smart device. It should be noted that the optical systems described are merely exemplary and other optical systems can be similarly aligned, for example, with an adapter such as 1500 to permit separate operating modes.

Figure 20:
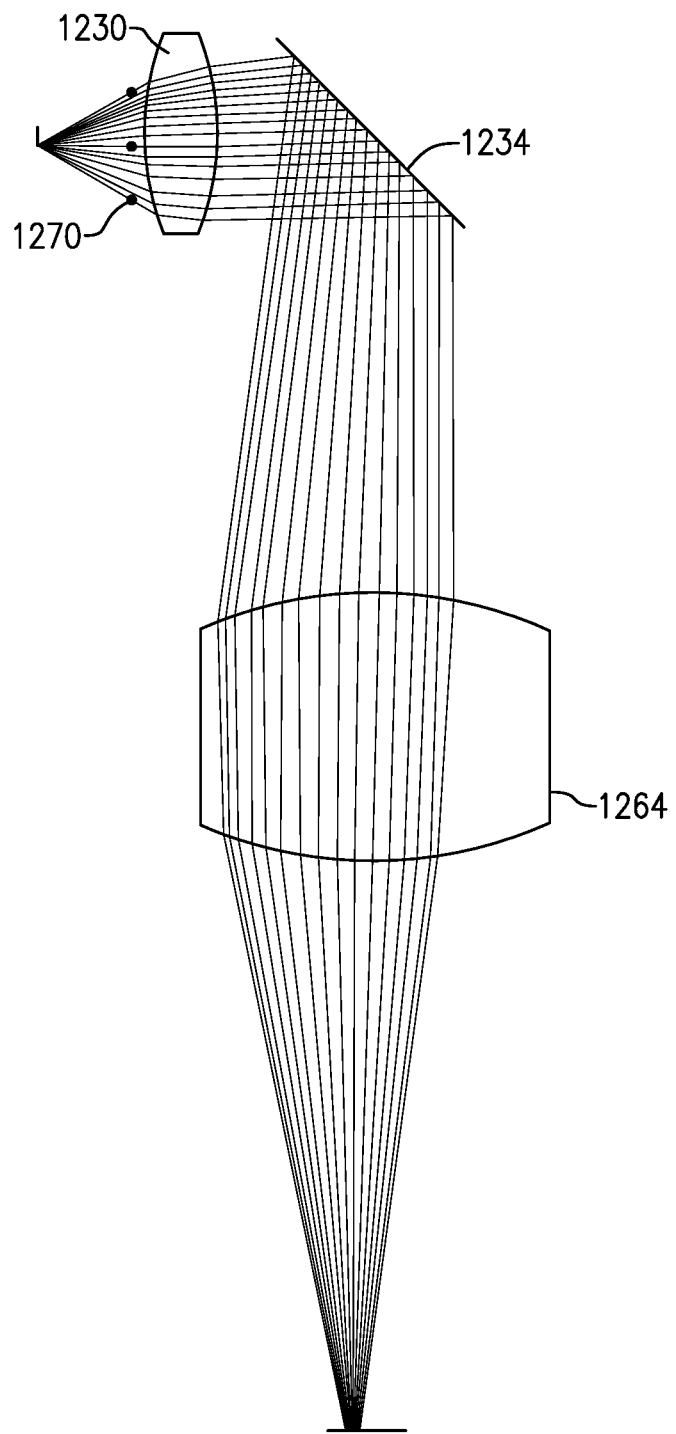
FIG. 20 is a schematic diagram of an optical layout for an illumination system of a stand-alone medical diagnostic or examination device in accordance with another embodiment.

With additional reference to FIGS. 16 and 17, FIG. 20 illustrates an optical layout of the corresponding off-axis illumination system. Light from the contained light source 1260, such as an LED or an incandescent bulb is directed through a condenser lens 1264 along a defined illumination axis 1268 and reflected from the angled surface of the beamsplitter 1234. This light is then further directed through the objective lens 1230 and is focused at the eye of the patient 1280. According to this version, a series of fixation lights 1270 are provided at the distal end of the instrument head. The number of fixation lights used can be varied. According to one example, at least two fixation lights can be provided that are diametrically opposed about the distal aperture of the instrument 1200 that are separately operated from the contained illumination source 1260. In terms of operation, the caregiver would move the device toward the eye of the patient and activate one of the fixation lights 1270. The patent would be requested to concentrate his or her vision on the fixation light 1270. By including multiple fixation lights, different portions of the retina can be examined by requesting the patient focus on the fixation lights in sequence and obtain measurements. In one example, a ringlet of several fixation lights could be disposed in which the images obtained using a smart device or other can be stitched and effectively cover a larger portion of the retina (15-30 degrees or more, enabling the determination of diabetic retinopathy. In another version, various other eye-related diagnoses can be obtained such as, but not limited to hypertension (artery-to-vein ratio), macular degeneration, glaucoma, diabetes, and those relating to retinal detachments.

Figure 21:
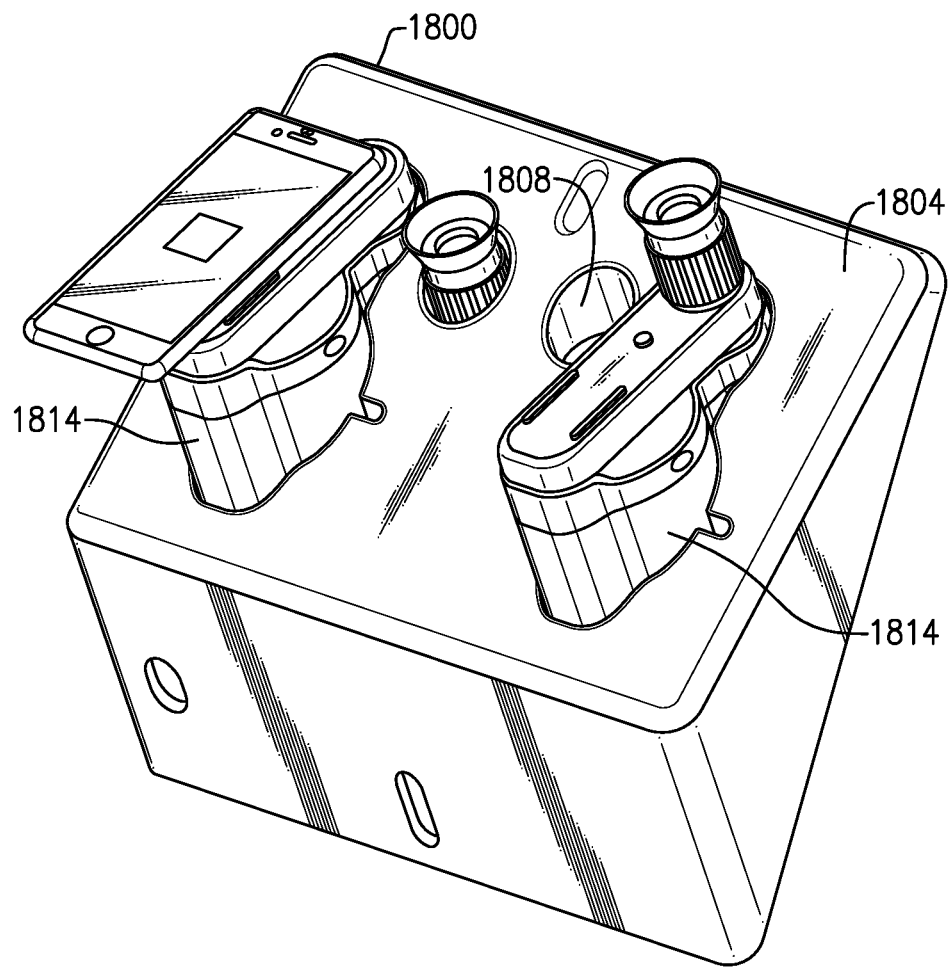
FIG. 21 is a perspective view of a mounting fixture in accordance with an embodiment for various components of the herein described medical examination system.

With reference to FIG. 21, each of the herein described instruments can be provided for access to a user in kit form, by defining a mounting unit 1800 that includes a plurality of slots 1808 formed in a support surface 1804 for accommodating various stand-alone medical diagnostic or examination devices 1814, as well as interchangeably mounted smart devices, adapters and eyepieces. Each of the various embodiments that are depicted can be provided for mounting to either a wall or similar structure (not shown) or can be mounted to other fixturing such as a movable cart in which the mounting can be permanent to releasable depending on the application. The mounting unit according to at least one version can include a supporting frame that is filled with a soft compliant material. The number of shaped slots formed in the filled compliant material can be are sized to receive, for example a pair of medical diagnostic or examination devices and accessories such as eyepieces and the like. The medical devices 1814 can be stored by positioning the distal end of the medical devices within the shaped slots 1808 with a portion of the devices 1814 being directly inserted into the slots 1808 and remaining portion being accessible, as needed, for removal by a user. The mounting units 1800 can be appropriately shaped with either the mounting surface 1804 or the supporting surfaces of the units 1800 being angled to provide additional versatility. In the depicted version, the mounting unit 1800 is configured to accommodate various forms of stand-alone medical devices, including versions previously discussed with reference to FIGS. 5(*a*)-6(*d*). It will be readily apparent to the person of sufficient skill in the field that other modifications and variations are possible, including versions in which the batteries of each of the retained instruments can be charged.

Figure 22A:
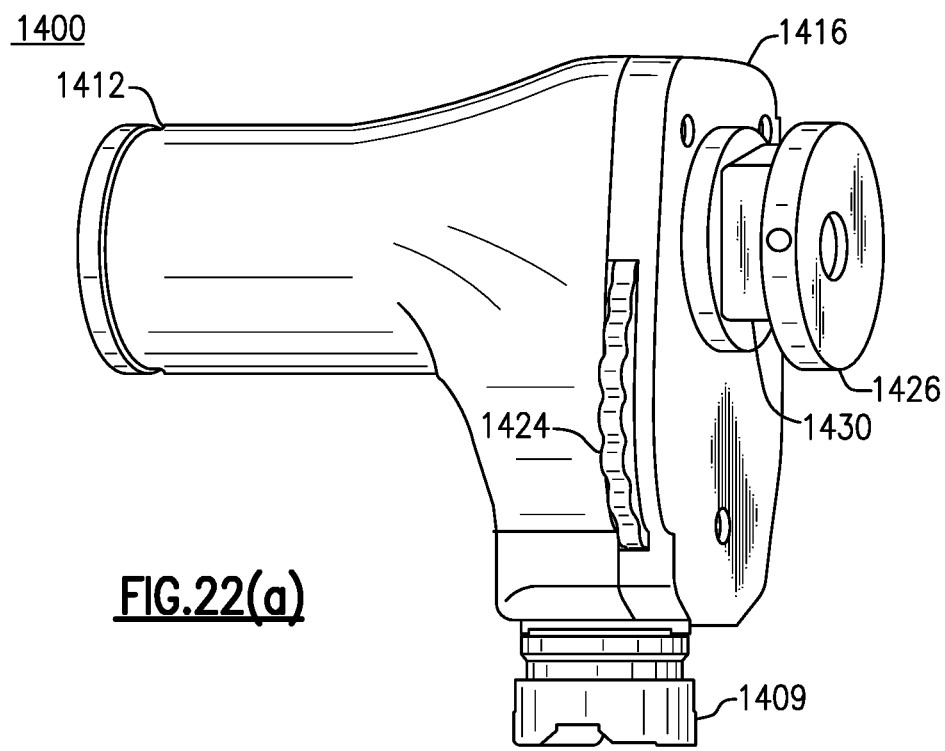
FIG. 22(a) is a side elevational view of another medical diagnostic or examination device in accordance with another embodiment.
Figure 22B:
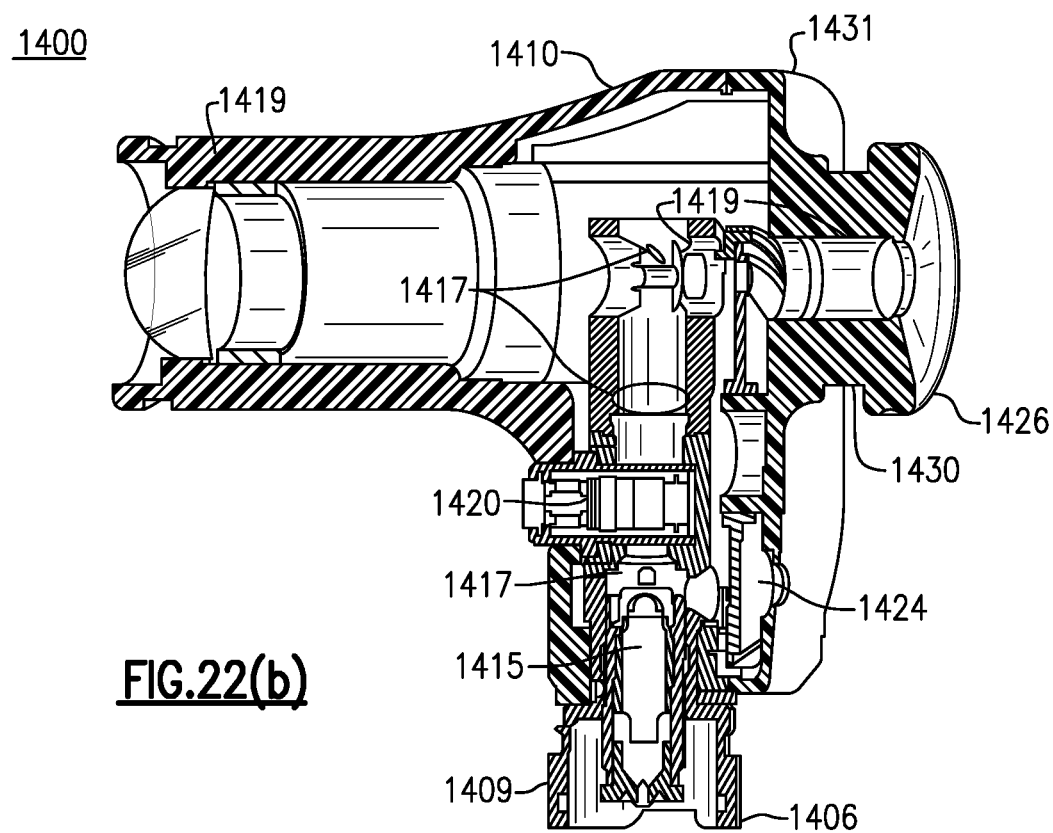
FIG. 22(b) depicts the medical device of FIG. 22(a) in section.

FIGS. 22(*a*) and 22(*b*) herein depict another medical examination device made in accordance with aspects of the present invention and more specifically an ophthalmoscope 1400. More specifically, the ophthalmoscope 1400 is defined by a handle portion 1406 (partially shown) and an instrument head 1410 that is releasably connected to a necked upper portion 1409 of the handle portion 1406. A light source 1415 forming a portion of an illumination system is powered by batteries (not shown) that are contained in the handle portion 1406. Optics are contained and aligned along respective optical and illumination axes within the interior of the instrument head 1410. The illumination axis extends upwardly from the contained light source 1415 through a number of optical elements 1417 including a rotatable aperture wheel 1420 formed in a lower portion of the instrument head 1410 in which light is directed to a distal end 1412 of the instrument head 1410 for directing to the eye of a patient (not shown). The optical system includes a series of optical elements 1419 that are aligned along an optical axis extending through the distal end 1412 and a proximal end 1416 of the instrument head 1410. A rotatable diopter wheel 1424 is also disposed along the defined optical axis near the proximal end 1416 of the device 1400. Additional details relating to an optical and illumination system useful with this design can be found in U.S. Patent Application Publication No. 2016/0073875A1 and U.S. Patent Application Publication No. 2015/0103317A1, the entire contents of which are herein incorporated by reference.

The proximal end 1416 of the herein described instrument 1400 can include an interface that permits the attachment of an adapter, such as previously described with regard to FIGS. 14(*a*)-15(*c*). More specifically, the proximal end 1416 of the instrument 1400 is defined by an outer lipped portion 1426, as well as a channel 1430 disposed between the lipped portion 1426 and a rear wall 1431 of the instrument head 1410. An adapter 1500, FIGS. 14(*a*)-14(*c*), as previously discussed, is defined by a supporting member having respective front and rear facing surfaces. The rear facing surface of the adapter 1500 includes a recessed area that is positioned to receive at least one interface plate of an attached smart device in a releasable fashion. As in the prior described embodiment, the adapter 1500 is further defined by an open-ended engagement portion that is sized and configured to engage the proximal end 1416 of the instrument 1400 with the lipped portion 1426 of the proximal end 1416 fitting within a formed channel of the open-ended device engagement portion and the channel 1430 of the proximal end fitting engaging a shoulder of the engagement portion. According to this embodiment, the channel 1430 is defined by four substantially flat sides to enable the adapter 1500 to be fitted in a plurality of mounting orientations. Alternatively, the channel can be defined by a cylindrical or other shaped surface. According to one version, detents can be provided to enable rotation of the attached smart device to a plurality of mounting orientations while still maintaining the optical alignment between the camera of the attached smart device and the optical system of the instrument 1400. Other suitable configurations such as flats in the channel can be contemplated for providing similar capabilities.

PARTS LIST FOR FIGS. 1-22(*b*)

10 stand-alone medical diagnostic or examination device (ophthalmoscope)
14 instrument housing
16 distal end
18 proximal end
20 frame or supporting structure
24 parallel channels or slots
32 smart device
100 alignment fixture
100A alignment fixture
104 interface plate
105 hole, interface plate
106 upper side, interface plate
107 slot, interface plate
108 raised platform
109A planar support surface
110A slot
111A pinhole
112 upper or top surface
116 legs
117 support flange
118 optical target
118A optical target
120 elongate slot
130A x-axis adjustment assembly
134A y-axis adjustment assembly
137A screw adjustment member
138A spring-loaded adjustment or support block
139A spring-loaded adjustment or support block
140 smart device
140A smart device
141A screw adjustment member
143A beam-like member
144 display
144A display
145A beam-like member
146 camera, smart device
148 target
148A target
149A image of optical target
160 otoscope
164 housing
169 rear or proximal opening
176 rear or proximal facing surface
180 spaced magnets
198 calibration target
200 stand-alone medical examination device
204 first interface plate
207 rear facing side, medical device
208 second interface plate
214 magnet
216 facing surface
217 magnet
220 smart device
223 front facing surface
300 medical diagnostic or examination device
303 distal end, device
305 back or proximal surface
309 magnetic interface
311 magnet
320 eyepiece
324 housing, eyepiece
326 proximal end, eyepiece
328 focusing knob, eyepiece
360 smart device
364 display, smart device
400 medical diagnostic or examination device
403 distal end, device
405 back or proximal surface, device
409 magnetic interface
412 magnet
500 medical diagnostic or examination device
503 distal end, device
504 body or housing
505 back or proximal surface, device
508 handle
509 magnetic interface
510 instrument head
511 magnet
600 medical diagnostic or examination device
603 distal end, device
604 body or housing
605 back or proximal surface, device
608 handle
609 magnetic interface
610 instrument head
611 magnet
700 otoscope
704 handle portion
706 upper necked portion
708 instrument head
710 eyepiece
711 distal end
712 conical insertion portion
713 slotted portion or slot
720 adapter
724 distal engaging portion
727 gusset
728 proximal supporting portion
732 resilient fingers
736 recessed slot
738 interface plate 740 through opening
750 smart device
754 display
758 connector or connector portion
800 ophthalmoscope
804 handle portion
806 necked portion
808 instrument head
810 eyepiece
813 slot or slotted portion
920 adapter
924 distal engaging portion
928 proximal supporting portion
929 open end
930 guide rails
932 resilient fingers
958 connector or connector portion
1000 otoscope
1004 housing
1008 handle
1010 instrument head
1012 distal end
1014 speculum tip element
1015 actuator knob
1020 adapter
1022 planar section, adapter
1024 eyepiece
1026 proximal facing or face surface
1027 housing, eyepiece
1029 distal facing surface, eyepiece
1036 slot, receiving
1050 smart device
1054 display
1100 ophthalmoscope
1104 housing
1108 handle portion
1110 instrument head
1112 distal end
1116 elastomeric eye cup
1120 adapter
1122 planar section
1124 eyepiece
1126 rear facing surface, adapter
1136 rear slot
1200 ophthalmoscope
1206 handle portion
1210 instrument head
1211 distal end
1213 proximal end
1220 adapter
1226 distal facing or face surface, adapter
1228 proximal facing surface, adapter
1230 objective lens
1234 beam splitter
1238 focusing/imaging lenses
1244 optical axis
1248 image sensor
1260 light source
1264 condenser lens
1268 illumination axis
1270 fixation lights
1280 eye, patient
1284 image sensor
1284 eyepiece
1288 fixed lenses
1292 aperture stop
1296 doctor's eye
1300 otoscope
1306 handle portion
1310 instrument head
1311 distal end
1313 proximal end
1320 adapter
1326 distal facing surface
1328 proximal facing surface
1332 distal lens
1336 speculum
1338 plano window
1342 field stop
1346 focusable objective lens
1348 second lens
1350 optical axis
1354 smart device
1362 doctor's eye
1364 fixed eyepiece lenses
1368 aperture stop
1400 ophthalmoscope
1406 handle portion
1409 upper necked portion
1410 instrument head
1412 distal end
1415 light source
1416 proximal end
1417 optical elements
1419 optical elements
1420 aperture wheel
1424 diopter wheel
1426 lipped portion
1430 channel
1431 rear wall, instrument head
1500 adapter
1504 supporting member or body
1507 forward or front facing side, adapter
1509 rear facing side, adapter
1511 magnets
1512 device connection portion
1515 outer surface
1517 cutout portion, outer surface
1519 through opening, supporting member
1520 center portion
1524 release lever
1530 shaped recess
1540 spring-loaded pin
1544 stop
1550 smart device
1554 aperture, camera
1560 medical examination device
1564 proximal receiving portion
1568 housing, device
1572 channel
1575 outer ringed portion
1580 eyepiece lens
1582 eyepiece lens
1590 browrest
1600 medical examination device
1604 proximal end
1608 shoulder, annular
1612 channel
1616 interior
1620 optical element
1624 seal
1628 opening, end
1700 medical examination device
1704 proximal end 1708 shoulder, annular
1712 channel
1716 interior
1720 optical element
1722 optical element
1726 opening, end
1800 mount
1804 support surface
1808 slots The invention is inclusive of combinations of the aspects described herein. References to "a particular aspect" (or "embodiment" or "version") and the like refer to features that are present in at least one aspect of the invention. Separate references to "an aspect" or "particular aspects" or the like do not necessarily refer to the same aspect or aspects; however, such aspects are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted.

The invention has been described in detail with particular reference to certain preferred aspects thereof, but it will be understood that variations, combinations, and modifications can be effected by a person of ordinary skill in the art within the intended spirit and scope of the invention.

The invention claimed is:

1. A medical examination system comprising:
    a medical device comprising:
        a housing, and
        an optical system disposed within an interior of the housing, the optical system being defined by an optical axis and configured to operate in an optical viewing mode using an eyepiece releasably attached to a proximal end of the housing;
    an adapter comprising:
        a distal connecting portion for enabling releasable attachment to the proximal end of the housing, and
        a proximal connecting portion configured to support one selected smart device from a plurality of different sized smart devices to enable a separate electronic viewing mode in lieu of the eyepiece, each smart device of the plurality of different sized smart devices having a camera and a display; and
    an alignment fixture separate from the adapter and the medical device, the alignment fixture having a mounting surface sized and configured to receive the selected smart device, the mounting surface having at least one opening and the alignment fixture having an integrated optical target; and
    the adapter further comprising at least one interface plate attached to a front facing side of the selected smart device through the at least one opening of the mounting surface of the alignment fixture following alignment of the camera of the selected smart device with the integrated optical target in which the integrated optical target is centered on the display of the selected smart device following planar movement on the mounting surface of the alignment fixture, the proximal connecting portion of the adapter being configured for engaging the one or more attached interface plates following removal of the selected smart device from the alignment fixture, such that the camera of the selected smart device is aligned with the optical axis of the medical device upon attachment of the distal connecting portion of the adapter to the proximal end of the housing.

2. The system according to claim 1, in which the proximal end of the housing includes a proximal receiving portion that is configured to releasably engage the distal connecting portion of the adapter.

3. The system according to claim 2, in which the distal connecting portion of the adapter includes an opening that is configured for alignment with the optical system of the medical device when the adapter is attached thereto.

4. The system according to claim 2, in which the adapter includes a lever configured for releasing the adapter from the medical device.

5. The system according to claim 4, in which the distal connecting portion includes a spring-loaded pin that is movable into and out of a defined recess sized to engage the proximal receiving portion of the medical device, wherein the lever is movable to a position to release the pin and assist in releasing the adapter from the medical device.

6. The system according to claim 2, in which the adapter is selectively and rotatably movable to a plurality of mounting orientations relative to the optical axis when the distal connecting portion of the adapter is attached to the proximal receiving portion of the medical device, the proximal receiving portion including a lipped portion having a larger diameter than an adjacent portion having a plurality of flats disposed on respective sides thereof.

7. The system according to claim 1, in which the adapter is configured to position a camera aperture of the selected smart device at the convergence point of the optical system, thereby placing the selected smart device in the same position in the electronic operating mode as that of the viewer's eye in the optical viewing mode.

8. The system according to claim 2, further comprising a plurality of medical devices, each of the medical devices having a proximal receiving portion configured for engaging the distal connecting portion of the adapter.

9. The system according to claim 1, in which the at least one interface plate is made from metal and the adapter includes at least one magnet disposed on a supporting surface for releasably securing the at least one interface plate.

10. A system enabling one or more medical devices to retain a selected one of a plurality of different sized smart devices, the system including an adapter comprising:
    a planar support surface configured to retain a selected smart device from the plurality of different sized smart devices,
    a device connecting portion distally extending from the planar support surface, and
    at least one interface plate configured to be positioned upon a front facing surface of the selected smart device using a separate alignment fixture of the system that aligns a digital camera of the selected smart device with an integrated optical target disposed on the alignment fixture, in which the at least one interface plate is attachable to a front facing side of the selected smart device via a defined opening in a mounting plate of the alignment fixture following alignment of the digital camera with the integrated optical target by movement of the selected smart device on the mounting plate of the alignment fixture until the integrated optical target is centered in a display of the selected smart device, in which the at least one interface plate, as attached to the front facing side of the selected smart device following alignment, is supported by the planar support surface that aligns the digital camera of the selected smart device with a formed opening of the device connecting portion of the adapter that further aligns the digital camera of the attached smart device with an optical system of a medical device when the device connecting portion engages the medical device.

11. The system of claim 10, in which the device connecting portion is configured to enable a supported smart device to assume a plurality of rotatable mounting orientations about an optical axis of a medical device to which the adapter is attached.

12. The system according to claim 11, including at least one feature for releasing the adapter from the medical device and in which the feature for releasing comprises a lever.

13. The system according to claim 10, in which the portion of the planar support surface includes at least one magnet positioned for engaging the at least one interface plate positioned on a smart device.

14. A medical examining system comprising:
a first medical device having a distal end, a proximal end and an optical system aligned along a first optical axis extending through the distal end and the proximal end of the first medical device;
a second medical device having a distal end, a proximal end and an optical system aligned along a second optical axis extending through the distal end and proximal end of the second medical device;
an adapter having a device connecting portion, each of the first and second medical examination devices having a proximal receiving portion configured for releasably engaging the device connecting portion of the adapter and in which the adapter includes an opening that is aligned with the optical axis of the first and second medical examination device when the adapter is attached thereto, the adapter further having a planar support surface configured to retain a smart device and at least one interface plate positioned on the smart device, and
an alignment fixture separate from the adapter and first and second medical devices, the alignment fixture having a mounting plate configured to support the smart device and including at least one opening, the alignment fixture further including an integrated optical target configured for alignment with a camera of the smart device in which the smart device is moved along the mounting plate until the integrated optical target is centered in a display of the smart device and enabling positioning of the at least one interface plate onto a front facing side of the smart device through the at least one opening following alignment with the integrated optical target and prior to removing the smart device from the alignment fixture, the positioning of the at least one interface plate on the smart device enabling the camera of the smart device to be further aligned with the device connecting portion of the adapter and the optical axis of either the first or second medical devices when the adapter is attached thereto.

15. The system according to claim 14, in which the first medical device is selected from one of the group of medical devices consisting of dermatoscopes, otoscopes, ophthalmoscopes, colposcopes, and rhinoscopes, and the second medical device is a device selected from one of the remainder of the group of medical devices.

\* \* \* \* \*